United States Patent
Handa et al.

(10) Patent No.: US 9,217,743 B2
(45) Date of Patent: Dec. 22, 2015

(54) SCREENING METHOD UTILIZING THALIDOMIDE-TARGETING FACTOR

(75) Inventors: Hiroshi Handa, Yokohama (JP); Hideki Ando, Yokohama (JP); Takumi Itoh, Yokohama (JP); Kentaro Hotta, Yokohama (JP)

(73) Assignees: Tokyo Institute of Technology, Tokyo (JP); Fujimoto Pharmaceutical Corporation, Osaka (JP)

( * ) Notice: Subject to any disclaimer, the term of this patent is extended or adjusted under 35 U.S.C. 154(b) by 0 days.

(21) Appl. No.: 13/498,067

(22) PCT Filed: Oct. 18, 2010

(86) PCT No.: PCT/JP2010/068272
§ 371 (c)(1),
(2), (4) Date: Mar. 23, 2012

(87) PCT Pub. No.: WO2011/049043
PCT Pub. Date: Apr. 28, 2011

(65) Prior Publication Data
US 2012/0192297 A1 Jul. 26, 2012

(30) Foreign Application Priority Data
Oct. 20, 2009 (JP) .................. 2009-241290

(51) Int. Cl.
*G01N 33/68* (2006.01)
*A01K 67/027* (2006.01)
*C07K 14/435* (2006.01)
*C12N 15/12* (2006.01)
*G01N 33/566* (2006.01)

(52) U.S. Cl.
CPC .......... *G01N 33/566* (2013.01); *G01N 2500/04* (2013.01)

(58) Field of Classification Search
CPC .................... G01N 2500/04; G01N 33/566
USPC ............... 436/86; 530/350; 536/23.5; 800/13
See application file for complete search history.

(56) References Cited

PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
An English translation of the International Preliminary Report on Patentability and Written Opinion of the International Searching Authority for International Application No. PCT/JP2010/068272, dated May 24, 2012.
Database UniProt, "RecName: Full=Protein cereblon;" Database accession No. Q96SW2, Dec. 1, 2001, 3 pages, XP002696670.
Database UniProt, "RecName: Full=Protein cereblon;" Database accession No. Q5R6Y2, Dec. 21, 2004, 1 page, XP002696671.
Extended European Search Report, dated Jun. 14, 2013, for Patent Application No. 10824892.3.
Sakamoto et al., "Development and Application of High Performance Affinity Beads: Toward Chemical Biology and Drug Discovery", The Chemical Record, vol. 9, 2009, pp. 66-85.
Aizawa, M., et al., "mRNA distribution of the thalidomide receptor, cereblon, in adult rat brain", Bulletinof the Japanese Society for Neurochemistry, Aug. 1, 2010, vol. 49, No. 2/3, p. 589.
Akira Murakami, "Around the functional food 54) Thalidomide no Hyoteki Bunshi", Food Style 21, Sep. 1, 2010, vol. 14, No. 9, pp. 66 to 67.
Fickentscher, K. et al., "Teratogenicity and embryotoxicity of thalidomide and 3-aza-thalidomide in mice", Pharmacology, 1974, vol. 11, No. 4, p. 193-198.
Hideki Ando et al., "Thalidomide Saikisei, Hyoteki Inshi no Dotei", Cell technology, Jul. 22, 2010, vol. 29, No. 8, pp. 812 to 813.
Hohberger,B.et al., "Cereblon is expressed in the retina and binds to voltage-gated chloride channels" ,FEBS Lett., Jan. 21, 2009, vol. 583, No. 4, p. 633-637.
Ito, T. et al., "Identification of a Primary Target of Thalidomide Teratogenicity", Science, Mar. 12, 2010, vol. 327, No. 5971, p. 1345-1350.
PCT/ISA/210—International Search Report dated Jan. 11, 2011, issued in PCT/JP2010/068272.
Schumacher, H.J., "Chemical structure and teratogenic properties",Proceedongs of the Guadeloupe Conf. "Methods Detect Environ Agents That Prod Congenital Defects", 1975, p. 65-77.
Takumi Ito et al., "Tsuini Kaimei! Thalidomide ga Okosu Saikisei no Nazo Hyoteki Bunshi Cereblon o Tsukitometa FG Beads", Chemistry, Aug. 1, 2010, vol. 65, No. 8, pp. 47 to 51.
Zimmerman, E.F., "Chemical structure and teratogenic mechanism of action", Proceedings of the Guadeloupe Conf. "Methods Detect Environ Agents That Prod Congenital Defects", 1975, p. 79-88.

* cited by examiner

*Primary Examiner* — Janet Epps-Smith
(74) *Attorney, Agent, or Firm* — Birch, Stewart, Kolasch & Birch, LLP

(57) ABSTRACT

With an aim to provide means for developing a compound devoid of teratogenicity but retaining beneficial actions, a screening method for a non-teratogenic substance comprising bringing a test substance into contact with cereblon or a fragment of cereblon, evaluating the bindability of the test substance with cereblon or the fragment of cereblon, and selecting a test substance that does not bind to cereblon or the fragment of cereblon or a test substance exhibiting lower bindability with cereblon or the fragment of cereblon than does thalidomide is provided.

12 Claims, 13 Drawing Sheets

Fig.12

```
Homo sapiens      1:MAGEGDQQDAAHNM---GNHLPLLPA---ESEEE-DEMEVEDQ-DSKEAKKPNI------  46
Mus musculus      1:M-------------KM---------MKL----------KWKLKTK-DSKEARKPDI------  23
Danio rerio       1:M---GN-------------QLQLLPE---NEEEE-EDDMETEDRDGEDVEKPSI------  34
D. melanogaster   1:MDEEENSEINSVQARDED-V-QLEDQQSQGLQDRQVDVIEQAWNNAMPDEPSPPAEDAFQ  58
A. thaliana       1:MDDERIRERERLQI---EQIRELDFE---ELQVEEVDDLHDSDSDDNNDDLSSF--P-FS  51

Homo sapiens     47:-------------INFDTSLPTSHTYL-GADMEEFHGRTLH---DDDSCQVIPVLPQVMM  89
Mus musculus     24:-------------INFDTSLPTSHTYL-GADMEEFHGRTLH---DDDSCRVIPVLPEVLM  66
Danio rerio      35:-------------INFDTSLPTSHAYL-GSDMEEFHGRTLH---DEDSVQNLPVLPHVAL  77
D. melanogaster  59:DPLATDGEGGDALEAMVENVLQDDTASEGSHPSSDMSLESPGSEDDSDLESLPHWMIPQN 118
A. thaliana      52:SHAQASGNLGDDELMFNPALASLHMYL-GEV-EDTQNRVSFV--DGGTVLKIPLFY-LEG 106

Homo sapiens     90:I-LIPGQT-LPLQLFHPQEVSMV-RNLIQKDRTFAVLAYSNVQ---EREAQF-GTTAEIY 142
Mus musculus     67:I-LIPGQT-LPLQLSHPQEVSMV-RNLIQKDRTFAVLGYSNVQ---EREAQF-GTTAEIY 119
Danio rerio      78:I-LIPGQT-LPLQLFRPQEVSMF-RNLVSQDRTFAVLAHSPDPSGTETKAEF-GTTAEIY 133
D. melanogaster 119:RLRSAV-DMM-VSQARNRDGGIAAL-LSGDNFLQRVRSMV-FSQERRRSRTSEETSQEAA 174
A. thaliana     107:VVLFPEAT-LPLRIIQPSFLAAVERALNQANAPSTIGVIRVYRRGAQFKYASVGTTAEIR 165

Homo sapiens    143:AYREEQDFGIEIVKVKAIGRQ------R-FKVLELRTQSDGIQQAKVQILPEC-------  188
Mus musculus    120:AYREEQEFGIEVVKVKAIGRQ------R-FKVLELRTQSDGIQQAKVQILPEC-------  165
Danio rerio     134:AFREEQEYGIETVKIKAVGRQ------R-FRVHEIRTQADGIRQAKVQILPER-------  179
D. melanogaster 175:EQPVDPPPQQPPRPPIDIGFDTNLPAEHSYFGNHL-SRVPGVDYLEVGSVHIMLIFLHQH 233
A. thaliana     166:QYRRLGDGSFNVITR---GQQ------R-FRLKHRWTDVEQFTCGEMQIVDEDVPLRTPR 215

Homo sapiens    189:-------------V---------L--PSTMSAVQL--E------S---------LNKCQI 207
Mus musculus    166:-------------V---------L--PSTMSAVQL--E------S---------LNKCQV 184
Danio rerio     180:-------------I---------L--PDPLCALQ----------F--------LPRLHT 196
D. melanogaster 234:ILFPGEVLPFM-IDGRMFDEDMPGLDGLIFGVSFPRLQPPEDNPHKLYGVTCQIYERGES 292
A. thaliana     216:DAFG-KLVPLSKLRGR-YPLGTASLSTPLRDMDAQSEANSEESFESALSPSEKRLHYSVV 273

Homo sapiens    208:FPSKPVSREDQCS--------YKWW-QKYQKRKFH--CANLT------------------ 238
Mus musculus    185:FPSKPISWEDQYS--------CKWW-QKYQKRKFH--CANLT------------------ 215
Danio rerio     197:HSPQTKHTQTTPP--------QKRCSQNYRQKKLH--CASMT------------------ 228
D. melanogaster 293:GRGLVFYKSRALQRIVINCDDIKG-SPQYIARNPTSKCFSKVKILP--E-YF-LPE-PLQ 346
A. thaliana     274:DSIFCNSTSSDDDQVVSTSTVQSSGSNPYSLRSIG--CLASSHDNENEDEQSAIGKTPVS 331

Homo sapiens    239:-------------------------S-WPRWLYSLYDAET-LMDRIKKQLREWDENL 268
Mus musculus    216:-------------------------S-WPRWLYSLYDAET-LMDRIKKQLREWDENL 245
Danio rerio     229:-------------------------S-WPPWVYSLYDSKT-LMSRVKKQLHEWDENL 258
D. melanogaster 347:TVDMGSMARFRDIPSMRDKYRRFQLSTTT-WPSDACQEYS-FSSIVERARQRL-ESQKID 403
A. thaliana     332:QEKYQKQNRLASFRQNTD-LSRFRMTPRAFWPFWAYRMFDSYY-LAQRAVD-L--WKQIV 386

Homo sapiens    269:KDDSLPS--N-PID-FSYRVAACLPIDDVLRI-QLLKIGSAIQRLRCELDIMNKCTSLCC 323
Mus musculus    246:KDDSLPE--N-PID-FSYRVAACLPIDDVLRI-QLLKIGSAIQALRCELDIMNKCTSLCC 300
Danio rerio     259:KDESLPT--N-PTD-FSYRVAACLPIDDALRL-QLLKIGSAIQRLRCELDIMDRCTSLCC 313
D. melanogaster 404:TMPKCPIQL--S-FWLVRNLHLTEKMM----RLTFLTDSVNT-RLQLIKSTFKDETLFFC 455
A. thaliana     387:GVPNMEAFVNKP-DILSFSIASKIPVSESIRQ-ELLELDGVSYRLQREIELLESFDRVRC 444

Homo sapiens    324:KQCQETEITT-KNEIFSLSLCGPMAAYVNPHGYVHETLIVYKACNLNLI--GRPSTEHSW 380
Mus musculus    301:KQCQETEITT-KNEIFSLSLCGPMAAYVNPHGYVHETLIVYKASNLNLI--GRPSTVHSW 357
Danio rerio     314:KQCQDTEITS-KNEIFSLSLYGPMAAYVNPHGYVHETLIVYKASNLNLI--GRPSTLHSW 370
D. melanogaster 456:RYCNSSLALCSDLFAMSKH--GVQTQYCNPEGYIHETNIVYRVISHAIGYSGEPSTKFSW 513
A. thaliana     445:IHCQTVI-ARRK-DMLVMSNEGPLGAYVNPHGYVHEIMIFYKANDIALR--GRPVKKDSW 500
                                                   * *

Homo sapiens    381:FPGYAWTVAQCKICASHIGWKFIATKKDMSPQKFWGLT----R-SALLPTIPDTEDEISP 435
Mus musculus    358:FPGYAWTIAQCKICASHIGWKFTATKKDMSPQKFWGLT----R-SALLPTIPETEDEISP 412
Danio rerio     371:FPGYAWTIAQCRTCSSHMGWKFSAVKKDLSFPRFWGLT----R-SALLPTIPQGEEGVEG 425
D. melanogaster 514:FPGYQWHIILCKFCAQHVGWEFKAVHPNLTEKVFGLAGSSVRIGKASEYSPFNGTTYVV 573
A. thaliana     501:FPGYAWTIANCATCETQLGWHFIATNKKLKPSSFWAV-----RGSQ-V---ADD------ 545

Homo sapiens    436:DKVILCL-----                                                442
Mus musculus    413:DKVILCL-----                                                419
Danio rerio     426:SRL-LCL-----                                                431
D. melanogaster 574:RNMMRMISSDME                                                585
A. thaliana     546:----MR------                                                547
```

Thalidomide    Phthalimide    Glutarimide    5HPP-33

SEQUENCE LISTING

<160> NUMBER OF SEQ ID NOS: 16

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence:synthetic
      oligonucleotide

<400> SEQUENCE: 1
cauaccuuga uaauguguu guguu                                              25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence:synthetic
      oligonucleotide

<400> SEQUENCE: 2
caguaaugaa caaggcuccu augua                                             25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence:synthetic
      oligonucleotide

<400> SEQUENCE: 3
gcaaagcaug uggauucaaa guuaa                                             25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence:synthetic
      oligonucleotide

<400> SEQUENCE: 4
gaaucucuga uagacagaga cuaua                                             25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 5
agagctgtag ctggttcccc atttc                                             25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 6
ctggtgctga acatcttctg ccatc                                             25

<210> SEQ ID NO 7
<211> LENGTH: 442
<212> TYPE: PRT
<213> ORGANISM: Homo sapiens

<400> SEQUENCE: 7

```
Met Ala Gly Glu Gly Asp Gln Gln Asp Ala Ala His Asn Met Gly Asn
1               5                   10                  15

His Leu Pro Leu Pro Ala Glu Ser Glu Glu Asp Glu Met Glu
            20                  25                  30

Val Glu Asp Gln Asp Ser Lys Glu Ala Lys Lys Pro Asn Ile Ile Asn
            35                  40                  45

Phe Asp Thr Ser Leu Pro Thr Ser His Thr Tyr Leu Gly Ala Asp Met
50                  55                  60

Glu Glu Phe His Gly Arg Thr Leu His Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
```

```
                    370                 375                 380
Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
                420                 425                 430

Ile Ser Pro Asp Lys Val Ile Leu Cys Leu
            435                 440

<210> SEQ ID NO 8
<211> LENGTH: 419
<212> TYPE: PRT
<213> ORGANISM: Mus musculus

<400> SEQUENCE: 8

Met Lys Met Met Lys Leu Lys Trp Lys Leu Lys Thr Lys Asp Ser Lys
1               5                   10                  15

Glu Ala Arg Lys Pro Asp Ile Ile Asn Phe Asp Thr Ser Leu Pro Thr
            20                  25                  30

Ser His Thr Tyr Leu Gly Ala Asp Met Glu Glu Phe His Gly Arg Thr
        35                  40                  45

Leu His Asp Asp Ser Cys Arg Val Ile Pro Val Leu Pro Glu Val
    50                  55                  60

Leu Met Ile Leu Ile Pro Gly Gln Thr Leu Pro Leu Gln Leu Ser His
65                  70                  75                  80

Pro Gln Glu Val Ser Met Val Arg Asn Leu Ile Gln Lys Asp Arg Thr
                85                  90                  95

Phe Ala Val Leu Gly Tyr Ser Asn Val Gln Glu Arg Glu Ala Gln Phe
            100                 105                 110

Gly Thr Thr Ala Glu Ile Tyr Ala Tyr Arg Glu Glu Gln Phe Gly
        115                 120                 125

Ile Glu Val Val Lys Val Lys Ala Ile Gly Arg Gln Arg Phe Lys Val
        130                 135                 140

Leu Glu Leu Arg Thr Gln Ser Asp Gly Ile Gln Gln Ala Lys Val Gln
145                 150                 155                 160

Ile Leu Pro Glu Cys Val Leu Pro Ser Thr Met Ser Ala Val Gln Leu
                165                 170                 175

Glu Ser Leu Asn Lys Cys Gln Val Phe Pro Ser Lys Pro Ile Ser Trp
            180                 185                 190

Glu Asp Gln Tyr Ser Cys Lys Trp Trp Gln Lys Tyr Gln Lys Arg Lys
        195                 200                 205

Phe His Cys Ala Asn Leu Thr Ser Trp Pro Arg Trp Leu Tyr Ser Leu
    210                 215                 220

Tyr Asp Ala Glu Thr Leu Met Asp Arg Ile Lys Lys Gln Leu Arg Glu
225                 230                 235                 240

Trp Asp Glu Asn Leu Lys Asp Asp Ser Leu Pro Glu Asn Pro Ile Asp
                245                 250                 255

Phe Ser Tyr Arg Val Ala Ala Cys Leu Pro Ile Asp Asp Val Leu Arg
            260                 265                 270

Ile Gln Leu Leu Lys Ile Gly Ser Ala Ile Gln Ala Leu Arg Cys Glu
        275                 280                 285

Leu Asp Ile Met Asn Lys Cys Thr Ser Leu Cys Cys Lys Gln Cys Gln
    290                 295                 300
```

```
Glu Thr Glu Ile Thr Thr Lys Asn Glu Ile Phe Ser Leu Ser Leu Cys
305                 310                 315                 320

Gly Pro Met Ala Ala Tyr Val Asn Pro His Gly Tyr Val His Glu Thr
            325                 330                 335

Leu Thr Val Tyr Lys Ala Ser Asn Leu Asn Leu Ile Gly Arg Pro Ser
            340                 345                 350

Thr Val His Ser Trp Phe Pro Gly Tyr Ala Trp Thr Ile Ala Gln Cys
            355                 360                 365

Lys Ile Cys Ala Ser His Ile Gly Trp Lys Phe Thr Ala Thr Lys Lys
            370                 375                 380

Asp Met Ser Pro Gln Lys Phe Trp Gly Leu Thr Arg Ser Ala Leu Leu
385                 390                 395                 400

Pro Thr Ile Pro Glu Thr Glu Asp Glu Ile Ser Pro Asp Lys Val Ile
            405                 410                 415

Leu Cys Leu

<210> SEQ ID NO 9
<211> LENGTH: 431
<212> TYPE: PRT
<213> ORGANISM: Danio rerio

<400> SEQUENCE: 9

Met Gly Asn Gln Leu Gln Leu Leu Pro Glu Asn Glu Glu Glu Glu Glu
1               5                   10                  15

Asp Asp Met Glu Thr Glu Asp Arg Asp Gly Glu Asp Val Glu Lys Pro
            20                  25                  30

Ser Ile Ile Asn Phe Asp Thr Ser Leu Pro Thr Ser His Ala Tyr Leu
            35                  40                  45

Gly Ser Asp Met Glu Glu Phe His Gly Arg Thr Leu His Asp Glu Asp
        50                  55                  60

Ser Val Gln Asn Leu Pro Val Leu Pro His Val Ala Leu Ile Leu Ile
65              70                  75                  80

Pro Gly Gln Thr Leu Pro Leu Gln Leu Phe Arg Pro Gln Glu Val Ser
            85                  90                  95

Met Phe Arg Asn Leu Val Ser Gln Asp Arg Thr Phe Ala Val Leu Ala
            100                 105                 110

His Ser Pro Asp Pro Ser Gly Thr Glu Thr Lys Ala Glu Phe Gly Thr
            115                 120                 125

Thr Ala Glu Ile Tyr Ala Phe Arg Glu Glu Gln Glu Tyr Gly Ile Glu
            130                 135                 140

Thr Val Lys Ile Lys Ala Val Gly Arg Gln Arg Phe Arg Val His Glu
145             150                 155                 160

Ile Arg Thr Gln Ala Asp Gly Ile Arg Gln Ala Lys Val Gln Ile Leu
            165                 170                 175

Pro Glu Arg Ile Leu Pro Asp Pro Leu Cys Ala Leu Gln Phe Leu Pro
            180                 185                 190

Arg Leu His Thr His Ser Pro Gln Thr Lys His Thr Gln Thr Thr Pro
            195                 200                 205

Pro Gln Lys Arg Cys Ser Gln Asn Tyr Arg Gly Lys Lys Leu His Cys
            210                 215                 220

Ala Ser Met Thr Ser Trp Pro Pro Trp Val Tyr Ser Leu Tyr Asp Ser
225                 230                 235                 240

Lys Thr Leu Met Ser Arg Val Lys Lys Gln Leu His Glu Trp Asp Glu
            245                 250                 255
```

-continued

```
Asn Leu Lys Asp Glu Ser Leu Pro Thr Asn Pro Thr Asp Phe Ser Tyr
            260                 265                 270

Arg Val Ala Ala Cys Leu Pro Ile Asp Asp Ala Leu Arg Leu Gln Leu
        275                 280                 285

Leu Lys Ile Gly Ser Ala Ile Gln Arg Leu Arg Cys Glu Leu Asp Ile
    290                 295                 300

Met Asp Arg Cys Thr Ser Leu Cys Cys Lys Gln Cys Gln Asp Thr Glu
305                 310                 315                 320

Ile Thr Ser Lys Asn Glu Ile Phe Ser Leu Ser Leu Tyr Gly Pro Met
                325                 330                 335

Ala Ala Tyr Val Asn Pro His Gly Tyr Val His Glu Thr Leu Thr Val
            340                 345                 350

Tyr Lys Ala Ser Asn Leu Asn Leu Ile Gly Arg Pro Ser Thr Leu His
        355                 360                 365

Ser Trp Phe Pro Gly Tyr Ala Trp Thr Ile Ala Gln Cys Arg Thr Cys
    370                 375                 380

Ser Ser His Met Gly Trp Lys Phe Ser Ala Val Lys Lys Asp Leu Ser
385                 390                 395                 400

Pro Pro Arg Phe Trp Gly Leu Thr Arg Ser Ala Leu Leu Pro Thr Ile
                405                 410                 415

Pro Gln Gly Glu Gly Val Glu Gly Ser Arg Leu Leu Cys Leu
            420                 425                 430

<210> SEQ ID NO 10
<211> LENGTH: 585
<212> TYPE: PRT
<213> ORGANISM: D. melanogaster

<400> SEQUENCE: 10

Met Asp Glu Glu Glu Asn Ser Glu Ile Asn Ser Val Gln Ala Arg Asp
1               5                   10                  15

Glu Asp Val Gln Leu Glu Asp Gln Gln Ser Gln Gly Leu Gln Asp Arg
            20                  25                  30

Gln Val Asp Val Ile Glu Gln Ala Trp Asn Asn Ala Met Pro Asp Glu
        35                  40                  45

Pro Ser Pro Pro Ala Glu Asp Ala Phe Gln Asp Pro Leu Ala Thr Asp
    50                  55                  60

Gly Glu Gly Gly Asp Ala Leu Glu Ala Met Val Glu Asn Val Leu Gln
65                  70                  75                  80

Asp Asp Thr Ala Ser Glu Gly Ser His Pro Ser Ser Asp Met Ser Leu
                85                  90                  95

Glu Ser Pro Gly Ser Glu Asp Ser Asp Leu Glu Ser Leu Pro His
            100                 105                 110

Trp Met Ile Pro Gln Asn Arg Leu Arg Ser Ala Val Asp Met Met Val
        115                 120                 125

Ser Gln Ala Arg Asn Arg Asp Gly Gly Ile Ala Ala Leu Leu Ser Gly
    130                 135                 140

Asp Asn Phe Leu Gln Arg Val Arg Ser Met Val Phe Ser Gln Glu Arg
145                 150                 155                 160

Arg Arg Ser Arg Thr Ser Glu Asp Thr Ser Gln Glu Ala Ala Glu Gln
                165                 170                 175

Pro Val Asp Pro Pro Gln Gln Pro Pro Arg Pro Ile Asp Ile
            180                 185                 190

Gly Phe Asp Thr Asn Leu Pro Ala Glu His Ser Tyr Phe Gly Asn His
        195                 200                 205
```

Leu Ser Arg Val Pro Gly Val Asp Tyr Leu Glu Val Gly Ser Val His
210                 215                 220

His Met Leu Ile Phe Leu His Gln His Ile Leu Phe Pro Gly Glu Val
225                 230                 235                 240

Leu Pro Phe Met Ile Asp Gly Arg Met Phe Asp Glu Asp Met Pro Gly
            245                 250                 255

Leu Asp Gly Leu Ile Phe Gly Val Ser Phe Pro Arg Leu Gln Pro Pro
            260                 265                 270

Glu Asp Asn Pro His Lys Leu Tyr Gly Val Thr Cys Gln Ile Tyr Glu
        275                 280                 285

Arg Gly Glu Ser Gly Arg Gly Leu Val Phe Tyr Lys Ser Arg Ala Leu
    290                 295                 300

Gln Arg Ile Val Ile Asn Cys Asp Asp Ile Lys Gly Ser Pro Gln Tyr
305                 310                 315                 320

Ile Ala Arg Asn Pro Thr Ser Lys Cys Phe Ser Lys Val Lys Ile Leu
                325                 330                 335

Pro Glu Tyr Phe Leu Pro Glu Pro Leu Gln Thr Val Asp Met Gly Ser
            340                 345                 350

Met Ala Arg Phe Arg Asp Ile Pro Ser Met Arg Asp Lys Tyr Arg Arg
        355                 360                 365

Phe Gln Leu Ser Thr Thr Thr Trp Pro Ser Asp Ala Cys Gln Glu Tyr
    370                 375                 380

Ser Phe Ser Ser Ile Val Glu Arg Ala Arg Gln Arg Leu Glu Ser Gln
385                 390                 395                 400

Lys Ile Asp Thr Met Pro Lys Cys Pro Ile Gln Leu Ser Phe Trp Leu
                405                 410                 415

Val Arg Asn Leu His Leu Thr Glu Lys Met Met Arg Leu Thr Phe Leu
            420                 425                 430

Thr Asp Ser Val Asn Thr Arg Leu Gln Leu Ile Lys Ser Thr Phe Lys
        435                 440                 445

Asp Glu Thr Leu Phe Phe Cys Arg Tyr Cys Asn Ser Ser Leu Ala Leu
    450                 455                 460

Cys Ser Asp Leu Phe Ala Met Ser Lys His Gly Val Gln Thr Gln Tyr
465                 470                 475                 480

Cys Asn Pro Glu Gly Tyr Ile His Glu Thr Asn Thr Val Tyr Arg Val
                485                 490                 495

Ile Ser His Ala Ile Gly Tyr Ser Gly Glu Pro Ser Thr Lys Phe Ser
            500                 505                 510

Trp Phe Pro Gly Tyr Gln Trp His Ile Ile Leu Cys Lys Phe Cys Ala
        515                 520                 525

Gln His Val Gly Trp Glu Phe Lys Ala Val His Pro Asn Leu Thr Pro
    530                 535                 540

Lys Val Phe Phe Gly Leu Ala Gly Ser Ser Val Arg Ile Gly Lys Ala
545                 550                 555                 560

Ser Glu Tyr Ser Pro Phe Asn Gly Thr Thr Tyr Val Val Arg Asn Met
                565                 570                 575

Met Arg Met Ile Ser Ser Asp Met Glu
            580                 585

<210> SEQ ID NO 11
<211> LENGTH: 547
<212> TYPE: PRT
<213> ORGANISM: A. thaliana

<400> SEQUENCE: 11

```
Met Asp Asp Glu Arg Ile Arg Glu Arg Leu Gln Ile Glu Gln
1               5                   10                  15

Ile Arg Glu Leu Asp Phe Glu Glu Leu Gln Val Glu Val Asp Asp
                20                  25                  30

Leu His Asp Ser Asp Ser Asp Asn Asn Asp Asp Leu Ser Ser Phe
            35                  40                  45

Pro Phe Ser Ser His Ala Gln Ala Ser Gly Asn Leu Gly Asp Asp Glu
    50                  55                  60

Leu Met Phe Asn Pro Ala Leu Ala Ser Leu His Met Tyr Leu Gly Glu
65                  70                  75                  80

Val Glu Asp Thr Gln Asn Arg Val Ser Phe Val Asp Gly Gly Thr Val
                85                  90                  95

Leu Lys Ile Pro Leu Phe Tyr Leu Glu Gly Val Val Leu Phe Pro Glu
                100                 105                 110

Ala Thr Leu Pro Leu Arg Ile Ile Gln Pro Ser Phe Leu Ala Ala Val
                115                 120                 125

Glu Arg Ala Leu Asn Gln Ala Asn Ala Pro Ser Thr Ile Gly Val Ile
130                 135                 140

Arg Val Tyr Arg Glu Gly Ala Gln Phe Lys Tyr Ala Ser Val Gly Thr
145                 150                 155                 160

Thr Ala Glu Ile Arg Gln Tyr Arg Arg Leu Gly Asp Gly Ser Phe Asn
                165                 170                 175

Val Ile Thr Arg Gly Gln Gln Arg Phe Arg Leu Lys His Arg Trp Thr
                180                 185                 190

Asp Val Glu Gly Phe Thr Cys Gly Glu Val Gln Ile Val Asp Glu Asp
                195                 200                 205

Val Pro Leu Arg Thr Pro Arg Asp Ala Phe Gly Lys Leu Val Pro Leu
                210                 215                 220

Ser Lys Leu Arg Gly Arg Tyr Pro Leu Gly Thr Ala Ser Leu Ser Thr
225                 230                 235                 240

Pro Leu Arg Asp Met Asp Ala Gln Ser Glu Ala Asn Ser Glu Glu Ser
                245                 250                 255

Phe Glu Ser Ala Leu Ser Pro Ser Glu Lys Arg Leu His Tyr Ser Val
                260                 265                 270

Val Asp Ser Ile Phe Cys Asn Ser Thr Ser Ser Asp Asp Gln Val
                275                 280                 285

Val Ser Thr Ser Thr Val Gln Ser Ser Gly Ser Asn Pro Tyr Ser Leu
                290                 295                 300

Arg Ser Ile Gly Cys Leu Ala Ser Ser His Asp Asn Glu Asn Glu Asp
305                 310                 315                 320

Glu Gln Ser Ala Ile Gly Lys Thr Pro Val Ser Gln Glu Lys Tyr Gln
                325                 330                 335

Lys Gln Asn Arg Leu Ala Ser Phe Arg Gln Asn Thr Asp Leu Ser Arg
                340                 345                 350

Phe Arg Met Thr Pro Arg Ala Phe Trp Pro Phe Trp Ala Tyr Arg Met
                355                 360                 365

Phe Asp Ser Tyr Tyr Leu Ala Gln Arg Ala Val Asp Leu Trp Lys Gln
                370                 375                 380

Ile Val Gly Val Pro Asn Met Glu Ala Phe Val Asn Lys Pro Asp Ile
385                 390                 395                 400

Leu Ser Phe Ser Ile Ala Ser Lys Ile Pro Val Ser Glu Ser Ile Arg
                405                 410                 415
```

```
Gln Glu Leu Leu Glu Leu Asp Gly Val Ser Tyr Arg Leu Gln Arg Glu
                420                 425                 430

Ile Glu Leu Leu Glu Ser Phe Asp Arg Val Arg Cys Ile His Cys Gln
            435                 440                 445

Thr Val Ile Ala Arg Arg Lys Asp Met Leu Val Met Ser Asn Glu Gly
        450                 455                 460

Pro Leu Gly Ala Tyr Val Asn Pro His Gly Tyr Val His Glu Ile Met
465                 470                 475                 480

Thr Phe Tyr Lys Ala Asn Asp Ile Ala Leu Arg Gly Arg Pro Val Lys
                485                 490                 495

Lys Asp Ser Trp Phe Pro Gly Tyr Ala Trp Thr Ile Ala Asn Cys Ala
            500                 505                 510

Thr Cys Glu Thr Gln Leu Gly Trp His Phe Thr Ala Thr Asn Lys Lys
        515                 520                 525

Leu Lys Pro Ser Ser Phe Trp Ala Val Arg Gly Ser Gln Val Ala Asp
    530                 535                 540

Asp Met Arg
545

<210> SEQ ID NO 12
<211> LENGTH: 104
<212> TYPE: PRT
<213> ORGANISM: Homo sapiens
<220> FEATURE:
<221> NAME/KEY: misc_feature
<223> OTHER INFORMATION: thalidomide-binding region of human cereblon

<400> SEQUENCE: 12

Ser Leu Ser Leu Cys Gly Pro Met Ala Ala Tyr Val Asn Pro His Gly
1               5                   10                  15

Tyr Val His Glu Thr Leu Thr Val Tyr Lys Ala Cys Asn Leu Asn Leu
                20                  25                  30

Ile Gly Arg Pro Ser Thr Glu His Ser Trp Phe Pro Gly Tyr Ala Trp
            35                  40                  45

Thr Val Ala Gln Cys Lys Ile Cys Ala Ser His Ile Gly Trp Lys Phe
        50                  55                  60

Thr Ala Thr Lys Lys Asp Met Ser Pro Gln Lys Phe Trp Gly Leu Thr
65                  70                  75                  80

Arg Ser Ala Leu Leu Pro Thr Ile Pro Asp Thr Glu Asp Glu Ile Ser
                85                  90                  95

Pro Asp Lys Val Ile Leu Cys Leu
            100

<210> SEQ ID NO 13
<211> LENGTH: 104
<212> TYPE: PRT
<213> ORGANISM: Mus musculus
<220> FEATURE:
<221> NAME/KEY: misc_feature
<223> OTHER INFORMATION: thalidomide-binding region in mouse cereblon

<400> SEQUENCE: 13

Ser Leu Ser Leu Cys Gly Pro Met Ala Ala Tyr Val Asn Pro His Gly
1               5                   10                  15

Tyr Val His Glu Thr Leu Thr Val Tyr Lys Ala Ser Asn Leu Asn Leu
                20                  25                  30

Ile Gly Arg Pro Ser Thr Val His Ser Trp Phe Pro Gly Tyr Ala Trp
            35                  40                  45
```

```
Thr Ile Ala Gln Cys Lys Ile Cys Ala Ser His Ile Gly Trp Lys Phe
         50                  55                  60

Thr Ala Thr Lys Lys Asp Met Ser Pro Gln Lys Phe Trp Gly Leu Thr
 65                  70                  75                  80

Arg Ser Ala Leu Leu Pro Thr Ile Pro Glu Thr Glu Asp Glu Ile Ser
                 85                  90                  95

Pro Asp Lys Val Ile Leu Cys Leu
                100

<210> SEQ ID NO 14
<211> LENGTH: 103
<212> TYPE: PRT
<213> ORGANISM: Danio rerio
<220> FEATURE:
<221> NAME/KEY: misc_feature
<223> OTHER INFORMATION: thalidomide-binding region of zebrafish
      cereblon

<400> SEQUENCE: 14

Ser Leu Ser Leu Tyr Gly Pro Met Ala Ala Tyr Val Asn Pro His Gly
 1               5                  10                  15

Tyr Val His Glu Thr Leu Thr Val Tyr Lys Ala Ser Asn Leu Asn Leu
                 20                  25                  30

Ile Gly Arg Pro Ser Thr Leu His Ser Trp Phe Pro Gly Tyr Ala Trp
         35                  40                  45

Thr Ile Ala Gln Cys Arg Thr Cys Ser Ser His Met Gly Trp Lys Phe
         50                  55                  60

Ser Ala Val Lys Lys Asp Leu Ser Pro Pro Arg Phe Trp Gly Leu Thr
 65                  70                  75                  80

Arg Ser Ala Leu Leu Pro Thr Ile Pro Gln Gly Glu Glu Gly Val Glu
                 85                  90                  95

Gly Ser Arg Leu Leu Cys Leu
                100

<210> SEQ ID NO 15
<211> LENGTH: 109
<212> TYPE: PRT
<213> ORGANISM: D. melanogaster
<220> FEATURE:
<221> NAME/KEY: misc_feature
<223> OTHER INFORMATION: thalidomide-binding region of fly cereblon

<400> SEQUENCE: 15

Ser Lys His Gly Val Gln Thr Gln Tyr Cys Asn Pro Glu Gly Tyr Ile
 1               5                  10                  15

His Glu Thr Asn Thr Val Tyr Arg Val Ile Ser His Ala Ile Gly Tyr
                 20                  25                  30

Ser Gly Glu Pro Ser Thr Lys Phe Ser Trp Phe Pro Gly Tyr Gln Trp
         35                  40                  45

His Ile Ile Leu Cys Lys Phe Cys Ala Gln His Val Gly Trp Glu Phe
         50                  55                  60

Lys Ala Val His Pro Asn Leu Thr Pro Lys Val Phe Phe Gly Leu Ala
 65                  70                  75                  80

Gly Ser Ser Val Arg Ile Gly Lys Ala Ser Glu Tyr Ser Pro Phe Asn
                 85                  90                  95

Gly Thr Thr Tyr Val Val Arg Asn Met Met Arg Met Ile
                100                 105
```

```
<210> SEQ ID NO 16
<211> LENGTH: 89
<212> TYPE: PRT
<213> ORGANISM: A. thaliana
<220> FEATURE:
<221> NAME/KEY: misc_feature
<223> OTHER INFORMATION: thalidomide-binding region of thale cress
      cereblon

<400> SEQUENCE: 16

Val Met Ser Asn Glu Gly Pro Leu Gly Ala Tyr Val Asn Pro His Gly
1               5                   10                  15

Tyr Val His Glu Ile Met Thr Phe Tyr Lys Ala Asn Asp Ile Ala Leu
            20                  25                  30

Arg Gly Arg Pro Val Lys Lys Asp Ser Trp Phe Pro Gly Tyr Ala Trp
        35                  40                  45

Thr Ile Ala Asn Cys Ala Thr Cys Glu Thr Gln Leu Gly Trp His Phe
    50                  55                  60

Thr Ala Thr Asn Lys Lys Leu Lys Pro Ser Ser Phe Trp Ala Val Arg
65                  70                  75                  80

Gly Ser Gln Val Ala Asp Asp Met Arg
                85
```

SCREENING METHOD UTILIZING THALIDOMIDE-TARGETING FACTOR

TECHNICAL FIELD

The present invention relates to a screening method for a non-teratogenic substance such as a medicine, a pharmaceutical additive, a food, a food additive, and particularly, a non-teratogenic thalidomide derivative and a screening method for an antagonist of thalidomide using cereblon (may be abbreviated as CRBN), which is a target factor of thalidomide, or a fragment of CRBN. The present invention also relates to mutated CRBN that scarcely binds to thalidomide, but retains a function as a component of a ubiquitin ligase complex, a nucleic acid encoding this mutated CRBN, and in a non-human animal in which this nucleic acid is introduced and expressed.

BACKGROUND ART

During the late 1950s and early 1960s, thalidomide was sold as a sedative in over 40 countries and was often prescribed to pregnant women as a treatment for morning sickness. Before its teratogenic activity came to light and its use was discontinued, it was estimated that several thousands to ten thousands or more birth defects (malformation), including stillbirth, had occurred (Cited Literatures 1 to 3). Use of thalidomide by women in their third to eighth week of pregnancy causes birth defects such as limb, ear, cardiac, and gastrointestinal malformations, which are called thalidomide embryopathy (Cited Literatures 1 to 3). In particular, limb and ear malformations are frequent. The limb malformation, known as phocomelia, is characterized by shortening of legs and arms. The ear malformations are represented by anotia, microtia, and hearing loss. Despite considerable effort for determination of causes, little is known about how these developmental defects are induced. Previous studies have suggested thalidomide-induced oxidative stress and its anti-angiogenic action as a possible cause of teratogenicity (Cited Literatures 4 and 5). However, several important questions remain unanswered, such as what molecules are direct targets of thalidomide and how the target factors mediate the thalidomide-induced teratogenicity.

Meanwhile, a protein called CRBN is known as a candidate causative factor for mild mental retardation in humans (Non-Patent Document 1 and Cited Literature 11). While this protein has also been reported to bind to a protein called Damaged DNA Binding protein 1 (DDB1) (Non-Patent Document 2 and Cited Literature 12), its relationship with thalidomide has never been reported.

CITATION LIST

Non-Patent Document

Non-Patent Document 1: J. J. Higgins, J. Pucilowska, R. Q. Lombardi, J. P. Rooney, Neurology 63, 1927 (2004).
Non-Patent Document 2: S. Angers et al., Nature 443, 590 (2006).

DISCLOSURE OF THE INVENTION

Problems to be Solved by the Invention

Recently, thalidomide use has increased for the treatment of multiple myeloma and erythema nodosum leprosum which is a type of leprosy with accompanying pain (Cited Literatures 2, 3, 6 and 7). Although detailed mechanisms of its actions remain unclear, thalidomide has been known to exert favorable effects on these diseases. Due to its outstanding problem of teratogenicity, however, thalidomide is used only under strict control (Cited Literature 8), and elimination of the teratogenicity from thalidomide is earnestly desired for wider applications of beneficial effects of the drug.

The present invention was accomplished the technical background as described above, and an object of the present invention is to provide means for developing a non-teratogenic alternative medicine to thalidomide that retain beneficial pharmacological actions of the drug.

Means for Solving the Problems

The present inventors conducted intensive research to achieve the aforementioned object. As a result, we have found that thalidomide exerts its teratogenicity by binding to CRBN and inhibiting the activity of a ubiquitin ligase complex containing CRBN as a component. As described earlier, it has been already known that CRBN is a candidate causative factor for mild mental retardation in humans and CRBN binds to DDB1; however, the relationship between CRBN and thalidomide has been totally unknown. In view of the above, the finding that CRBN was a target of the thalidomide-induced teratogenicity was absolutely unpredictable at the time of filing of the present application.

Based on the above findings, the teratogenicity of a thalidomide derivative can be predicted by evaluating the binding affinity of the compound to CRBN.

Expanding this new finding, not only thalidomide derivatives but also all the test substances can be predicted whether they have thalidomide-like teratogenicity by examining their bindability with CRBN.

Also, the present inventors have found that amino acid residues from position 339 to position 442 from the N-terminus of human CRBN serve as a binding region for thalidomide and human CRBN in which tyrosine at position 384 and tryptophan at position 386 from the N-terminus are substituted with alanine has reduced bindability with thalidomide, but retains a function as a component of a ubiquitin ligase complex.

The present invention was accomplished based on the aforementioned findings.

That is, the present invention provides the following [1] to [11].

[1] A screening method for a non-teratogenic substance comprising bringing a test substance into contact with cereblon or a fragment of cereblon, evaluating the bindability of the test substance with cereblon or the fragment of cereblon, and selecting a test substance that does not bind to cereblon or the fragment of cereblon or a test substance exhibiting lower bindability with cereblon or the fragment of cereblon than does thalidomide.

[2] The screening method for a non-teratogenic substance according to [1], wherein the test substance is a medicine.

[3] The screening method for a non-teratogenic substance according to [1] or [2], wherein the test substance is a thalidomide derivative represented by the general formula (1):

[Formula 1]

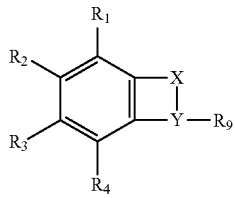

(1)

wherein, a compound in which X is $R_5$ to $R_7$ and Y is $R_6$ to $R_8$ is called Compound (A), a compound in which X is $R_5$ and Y is $R_6$ to $R_8$ is called Compound (B), and a compound in which X is $R_5$ and Y is $R_6$ is called Compound (C), and $R_1$, $R_2$, $R_3$, and $R_4$ each can be selected from —H; —OH; =O; linear and branched alkane, alkene and alkyne; cyclic alkane, alkene and alkyne; a combination of cyclic and non-cyclic alkane, alkene and alkyne; alcohol, aldehyde, ketone, carboxylic acid, ester or an ether moiety combining a ring and a non-ring or a combination of cyclic/non-cyclic moieties; aza; amino; -MOn or —O-MOn [wherein, M=N and n=2; M=S and n=2 or 3; or M=P and n=1 to 3]; and halogen; and $R_5$, $R_6$, $R_7$ and $R_8$ are each independently selected from the formula (2):

[Formula 2]

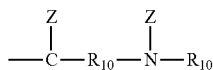

(2)

and —O— (wherein, Z is optional and defined in the same way as $R_1$ as described above); and $R_{10}$ is defined in the same way as $R_1$ as described above, or, (when Z is non-existent), $R_{10}$=O;

$R_9$ is a moiety having the formula (3), (4), (5), (6) or (7):

[Formula 3]

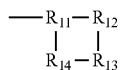

(3)

[Formula 4]

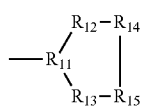

(4)

[Formula 5]

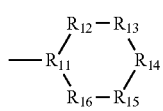

(5)

[Formula 6]

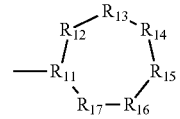

(6)

wherein, $R_{11}$ to $R_{17}$ are each (independently) defined in the same way as $R_5$ as described above, or

[Formula 7]

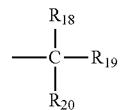

(7)

wherein, $R_{18}$, $R_{19}$ and $R_{20}$ are each independently selected from
H, —CH$_3$, —COOH, —CONH$_2$, —CH$_2$)n-COOH and —(CH$_2$)nCONH$_2$, wherein n=1 to 4.

[4] The screening method for a non-teratogenic substance according to any of [1] to [3], wherein, the fragment of cereblon has an amino acid sequence from position 339 to position 442 from the N-terminus of the amino acid sequence shown in SEQ ID NO: 7 and the rest of the amino acid sequence of SEQ ID NO: 7 having been subjected to substitution, deletion, and/or addition of one or more amino acid residues.

[5] The screening method for a non-teratogenic substance according to any of [1] to [4], wherein the cereblon or the fragment of cereblon is immobilized on a carrier.

[6] The screening method for a non-teratogenic substance according to [3], wherein the thalidomide derivative has pharmacological actions of thalidomide or a known thalidomide derivative.

[7] A screening method for a teratogenic substance antagonist comprising the step of bringing a test substance into contact with cereblon or a fragment of cereblon, evaluating the bindability of the test substance with cereblon or the fragment of cereblon, and selecting a test substance that binds to cereblon or the fragment of cereblon, and the step of selecting, from among the substances selected by the above step, a substance capable of attenuating i) teratogenicity or ii) an inhibitory action exerted on an activity of a cereblon-containing ubiquitin ligase complex.

[8] The screening method for a teratogenic substance antagonist according to [7], wherein the cereblon or the fragment of cereblon is immobilized on a carrier.

[9] A mutated cereblon comprising the following amino acid substitution (a) and/or (b);

(a) substitution of tyrosine at position 384 from the N-terminus of human cereblon or an equivalent amino acid with alanine; and (b) substitution of tryptophan at position 386 from the N-terminus of human cereblon or an equivalent amino acid with alanine.

[10] A nucleic acid encoding the mutated cereblon according to [9].

[11] A thalidomide-induced teratogenicity-resistant non-human animal having introduced therein the nucleic acid according to [10] as a gene and expressing the gene.

Advantages of the Invention

The non-teratogenic substance obtained by the screening method of the present invention is capable of predicting the presence or absence of thalidomide-like teratogenicity, and the non-teratogenic thalidomide derivative is useful as an alternative medicine to thalidomide. Also, the antagonist of thalidomide obtained by the screening method of the present invention acts to reduce the teratogenic risk of thalidomide.

The animal having introduced therein a nucleic acid encoding the mutated CRBN of the present invention as a gene and expressing the gene exhibits resistance against the thalidomide-induced teratogenicity, and thus is useful for evaluations of the pharmacological effect of thalidomide, and the like.

BRIEF DESCRIPTION OF THE DRAWINGS

FIG. 11 shows the relationship of CRBN deletion mutants and the formation of ubiquitin complex. (A) Schematic representation of CRBN and its deletion mutant. (B) FH-CRBN (wild type) and its mutants were expressed in 293T cells and immunoprecipitated with anti-FLAG antibody. CRBN, and its mutant, and endogenous DDB1 bound to them were detected by western blotting. As a result, it was revealed that deletion of amino acids from position 187 to position 260 of CRBN (ΔMid) abolished its interaction with DDB1. (C) CRBN and ΔMid, a mutant lacking the amino acids from position 187 to position 260, were expressed in 293T cells. After immunoprecipitating with anti-FLAG antibody, DDB1 and Cul4A bound to CRBN or ΔMid were analyzed by Western blotting. The ΔMid was incapable of forming a complex with DDB1 and Cul4a.

FIG. 12 (SEQ ID NOS: 7-11) relates to the evolutionary conservation of CRBN. Amino acid sequences of CRBN orthologs from five species were aligned. The boxed amino acids are those that are fully conserved among these species. Arrow indicates the thalidomide-binding region determined by deletion mutant analysis, whereas asterisks indicate amino acids that are critical for thalidomide binding (Y384 and W386). See FIG. 3.

BEST MODE FOR CARRYING OUT THE INVENTION

Figure 1:
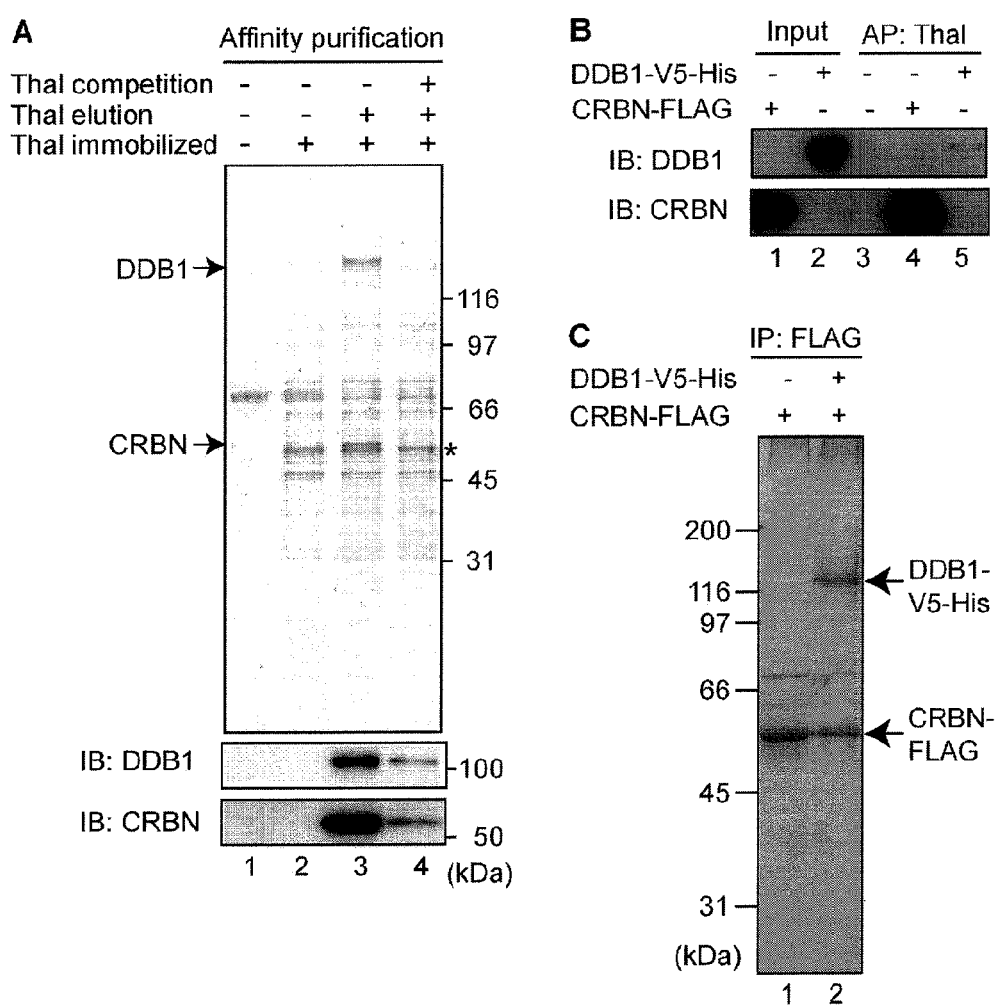
FIG. 1 relates to the bindability of thalidomide (thal) with CRBN and DDB1. (A) Thalidomide-binding proteins were purified from HeLa cell extracts by using thalidomide-immobilized (+) or control (−) beads. Bound proteins were eluted by addition of thalidomide. Eluted proteins were subjected to electrophoresis and then silver staining (upper panel). Asterisk (*) indicates non-specific binding. The bound proteins were identified as CRBN and DDB1 by tandem mass spectrometry and Western blotting. When 0.3 mM thalidomide was added to extract before incubation with the beads, the yield of these proteins were reduced. (B) To determine whether the protein bound to thalidomide-immobilized beads was CRBN or DDB1, purified recombinant FLAG-epitope tagged CRBN (CRBN-FLAG) and V5 and His-epitope tagged DDB1 (DDB1-V5-His) were mixed with thalidomide-immobilized beads. Bound proteins were detected by the western blotting. As a result, the protein bound to the beads was CRBN. (C) CRBN-FLAG and DDB1-V5-His were simultaneously or independently expressed in Sf9 cells and immunoprecipitated with anti-FLAG antibody. The precipitated protein was subjected to electrophoresis and Coomassie staining. As a result, DDB1 was detected.

Hereinbelow, the present invention will be described in detail.

(1) The Screening Method for a Non-Teratogenic Substance

The screening method for a non-teratogenic substance of the present invention comprises bringing a test substance into contact with CRBN or a fragment of CRBN, evaluating the bindability of the test substance with CRBN or the fragment of CRBN, and selecting a test substance that does not bind to CRBN or the fragment of CRBN or a test substance exhibiting lower bindability with CRBN or the fragment of CRBN than does thalidomide.

Selection of a test substance exhibiting lower bindability with CRBN and its fragment than does thalidomide can be carried out by, for example, performing a control experiment using thalidomide in place of the test substance and comparing the bindability of the test substance to that of thalidomide.

CRBN is considered to be a target molecule of the thalidomide-induced teratogenicity. Therefore, a substance that does not bind to CRBN or a substance exhibiting lower bindability than does thalidomide is considered to be devoid of teratogenicity of thalidomide or have attenuated teratogenicity.

Although no particular limitation is imposed on the test substance, it is preferably a substance administered to or fed by humans or other animals, and examples thereof include a medicine, a pharmaceutical additive, a food, a food additive, or a chemical contained in these substances.

Thalidomide derivatives are important among the medicines.

Examples of the thalidomide derivative include a compound represented by the following general formula (1):

General Formula (1)

[Formula 8]

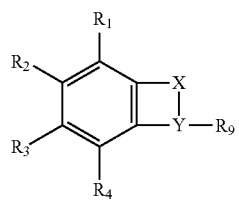

(1)

wherein, a compound in which X is $R_5$ to $R_7$ and Y is $R_6$ to $R_8$ is called Compound (A), a compound in which X is $R_5$ and Y is $R_6$ to $R_8$ is called Compound (B), and a compound in which X is $R_5$ and Y is $R_8$ is called Compound (C), and $R_1$, $R_2$, $R_3$, and $R_4$ each can be selected from —H; —OH; =O; linear and branched alkane, alkene and alkyne; cyclic alkane, alkene and alkyne; a combination of cyclic and non-cyclic alkane, alkene and alkyne; alcohol, aldehyde, ketone, carboxylic acid, ester or an ether moiety combining a ring and a non-ring or a combination of cyclic/non-cyclic moieties; aza; amino; -MOn or —O-MOn [wherein, M=N and n=2; M=S and n=2 or 3; or M=P and n—1 to 3]; and halogen; and $R_5$, $R_6$, $R_7$ and $R_8$ are each independently selected from the formula (2):

[Formula 9]

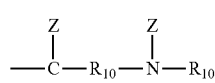

(2)

and —O— (wherein, Z is optional and defined in the same way as $R_1$ as described above); and $R_{10}$ is defined in the same way as $R_1$ as described above, or, (when Z is non-existent), $R_{10}$=O;

$R_9$ is a moiety having the formula (3), (4), (5), (6) or (7):

[Formula 10]

(3)

[Formula 11]

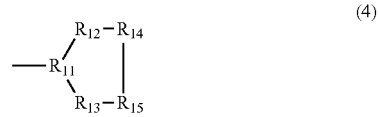

(4)

[Formula 12]

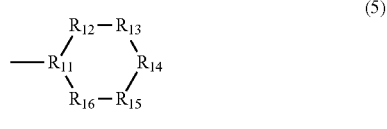

(5)

[Formula 13]

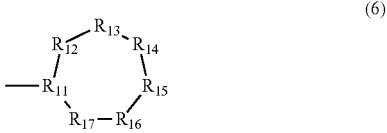

(6)

wherein, $R_{11}$ to $R_{17}$ are each (independently) defined in the same way as $R_5$ as described above, or

[Formula 14]

(7)

wherein, $R_{18}$, $R_{19}$ and $R_{20}$ are each independently selected from

H, —CH$_3$, —COOH, —CONH$_2$, —CH$_2$)n-COOH and —(CH$_2$)nCONH$_2$, wherein n=1 to 4.

Among the thalidomide derivatives, 5-hydroxy-(2,6-diisopropylphenyl)-1H-isoindole-1,3-dione (5HPP-33) was confirmed to have extremely low bindability with cereblon, while having pharmacological actions such as growth inhibition of human myeloma cells.

As the thalidomide derivative, one having pharmacological actions of thalidomide or known thalidomide derivatives is preferred.

As the pharmacological actions of thalidomide, the followings have been reported. (i) suppressing bFGF-induced angiogenesis; (ii) suppressing TNF-α production by LPS-stimulated human monocytes and IL-6 production by coculture of tumor cells such as human myeloma cells and human bone marrow stromal cells; (iii) increasing the number of natural killer cells in peripheral blood of multiple myeloma patients, enhancement of IL-2 and INF-γ production after T cell receptor stimulation, and promoting IL-2-dependent T cell proliferation; and (iv) inducing apoptosis and growth inhibition of tumor cells such as human myeloma cells.

Further, examples of the preventive or therapeutic effect of thalidomide on disease include a sedative, leprosy (specifically, erythema nodosum leprosum), transplantation disease, multiple myeloma, solid cancer, systemic lupus erythematosus, multiple sclerosis, Behcet's disease and inflammatory bowel disease (Crohn's disease and ulcerative colitis) are include. Examples of the pharmacological action of known thalidomide derivatives include therapeutic actions of lenalidomide on multiple myeloma and myelodysplastic syndrome (MDS), and therapeutic actions of pomalidomide on multiple myeloma and myelofibrosis are include.

CRBN is a already known protein, and the base sequence of the gene encoding CRBN(CRBN gene) is also published in a database. For example, the base sequences of human, mouse, rat and zebrafish CRBN gene are registered in Entrez Gene under Gene ID: 51185, Gene ID: 58799, Gene ID: 297498 and Gene ID: 445491, respectively. As the CRBN and the CRBN gene, naturally derived ones may be used, while mutated CRBN composed of an amino acid sequence of naturally-derived CRBN having been subjected to deletion, substitution or addition of one or several CRBN mutants that are capable of forming an active ubiquitin ligase complex and a gene encoding this mutated CRBN may also be used.

The present inventors have specified the thalidomide-binding region in the human-derived CRBN. Accordingly, even if a fragment of CRBN containing the thalidomide-binding region is used instead of CRBN, the bindability can still be evaluated. Examples of the thalidomide-binding region include a region of the C-terminal 104 amino acids of human-derived CRBN. In CRBN derived from non-human organisms, a region corresponding to the aforementioned region of C-terminal 104 amino acids (that is, a region that matches a region of the C-terminal 104 amino acids of human CRBN when aligned based on the amino acid identity) can be used as the thalidomide-binding region.

Examples of the fragment of CRBN include a fragment of cereblon having an amino acid sequence from 339 to 442 from the N-terminus of the amino acid sequence shown in SEQ ID NO: 7 and the rest of the amino acid sequence of SEQ ID NO: 7 having been subjected to substitution, deletion, and/or addition of one or more amino acid residues, and a fragment of CRBN derived from various organisms corresponding to the aforementioned fragment of human CRBN. Also, CRBN and the fragments of CRBN can be provided as fusion protein by adding other proteins.

Although CRBN or the fragment of CRBN used in the present invention may be any of the aforementioned CRBN derived from various organisms, mutated CRBN and fragments of these CRBNs, in view of the object of the present invention of acquiring thalidomide derivatives that are non-teratogenic to humans, the use of human CRBN or a fragment of human-derived CRBN is favorable.

It is preferable to immobilize CRBN and the fragment of CRBN on a carrier. Although the carrier is not particularly limited as long as it can immobilize CRBN and the fragment of CRBN, a particulate material is preferred, and also, a magnetic carrier is preferred. Examples of the preferred carrier include magnetic nano beads coated with an organic polymer. Although the particle diameter of the magnetic nano beads coated with an organic polymer is not particularly limited, it is preferably 1 to 500 nm, more preferably 20 to 300 nm. Examples of the organic polymer include GMA, a copolymer of GMA and styrene, (poly)methacrylic acid and (poly)acrylic acid. Specific examples of the magnetic nano beads coated with an organic polymer include SG beads (Kawaguchi et al., Nucleic Acids Research 1989, 17: 6229 to 6240), FG beads (Nishio et al., Colloids and Surfaces B: Biointerfaces 2008, 64: 162 to 169), Dynabeads, Adembeads and nanomag.

Evaluation of the bindability of a thalidomide derivative with CRBN can be carried out by a routine method, for example, by surface plasmon resonance using BIAcore or isothermal titration calorimetry (ITC).

Although the screening method of the present invention is not particularly limited as long as it enables evaluation of the bindability of a test substance with CRBN or a fragment of CRBN, for example, it can be performed as follows.

(A) Screening Method Using FG Beads

Firstly, thalidomide-immobilized FG beads are prepared. The immobilized beads are mixed and incubated with extracts of CRBN-expressing cells or recombinant proteins for one hour or longer in a rotator at 5 rpm and 4° C. Then, after the beads are washed with a buffer, for example, a buffer containing a thalidomide derivative as a test substance is passed through the beads to see whether CRBN is eluted. Examples of a detection method include Western blotting, dot blotting, CBB staining, and silver staining. Thalidomide and phthalimide, which is confirmed to be non-binding, are used as control samples. Also, the use of Target Angler series, which is an FG bead-screening instrument supplied by Tamagawa Seiki Co., Ltd., enables analysis of a large amount of samples.

(B) Screening Using BIAcore

Firstly, CRBN having a functional group such as an amino group or a carboxyl group is immobilized on a BIAcore sensor chip. Then, various derivatives are passed through a BIAcore measuring instrument (GE Healthcare) such as BIAcore 3000 in which the immobilized chip has been set and the dissociation constant is measured. Thalidomide and phthalimide are used as control experiments.

(C) Screening Using Isothermal Titration Calorimetry

A solution containing a thalidomide derivative is added dropwise several tens of times (for example, 18 times) to a solution containing CRBN in a sample cell. By plotting the calories generated at each concentration against the mole ratio of the derivative to CRBN in the cell, a binding isotherm for the interaction is obtained. The dissociation constant is calculated from the binding isotherm thus obtained. Thalidomide and phthalimide are used as control experiments.

(2) Screening Method for a Teratogenic Substance Antagonist

The screening method for a teratogenic substance antagonist of the present invention comprises the step of bringing a test substance into contact with CRBN or a fragment of CRBN by mixing or the like, evaluating whether or not the test substance binds to CRBN or the fragment of CRBN, and selecting a test substance that binds to CRBN or the fragment of CRBN, and the step of selecting, from among the substances selected by the above step, a substance capable of attenuating i) teratogenicity or ii) an inhibitory action on a ubiquitin ligase complex containing CRBN.

The antagonist of a teratogenic substance such as thalidomide obtained by the method above inhibits binding of a teratogenic substance to CRBN. Accordingly, when a subject takes a teratogenic substance such as thalidomide and its derivatives, the risk of teratogenicity can be reduced by the concomitant use of this antagonist.

The first half of the steps, i.e., the step of bringing a test substance into contact with CRBN or a fragment of CRBN, evaluating whether or not the test substance binds to CRBN or the fragment of CRBN, and selecting a test substance that binds to CRBN or the fragment of CRBN, can be performed in a similar manner to the screening method of (1).

When the substance selected by the first half of the steps is not an agonist but an antagonist, it should attenuate the action exerted by a teratogenic substance such as thalidomide. Accordingly, a teratogenic substance antagonist can be selected by evaluating whether or not the substance attenuates teratogenicity or the inhibitory action exerted on the activity of a ubiquitin ligase complex containing CRBN.

Examples of the action exerted by thalidomide include, in addition to its previously known teratogenicity, the inhibitory action exerted on the activity of a ubiquitin ligase complex as revealed by the present inventors this time.

Whether or not a test substance attenuates the action exerted by thalidomide can be confirmed by comparing the action of thalidomide in the presence and absence of a test substance.

Although the screening method for a teratogenic substance antagonist of the present invention is not particularly limited, for example, it can be performed as follows.

Firstly, it is confirmed whether or not an antagonist candidate binds to CRBN. The method for confirming the binding is similar to the screening method of (1). The antagonist candidates shown to significantly bind to CRBN in this step are then screened by the following methods.

(A) Effect on Ubiquitination In Vitro

An antagonist candidate and thalidomide are added to 293T cells expressing FH-CRBN. Then, the amount of ubiquitinated protein in the extracts of the cells is determined by Western blotting. At this time, if reduction in the amount of ubiquitinated protein is suppressed to a greater extent by the addition of the antagonist candidate compared to the addition of thalidomide alone, then the antagonist candidate is determined to be an antagonist.

(B) Screening Using Zebrafish

Dechorionated zebrafish embryos are allowed to develop in media containing thalidomide and an antagonist candidate. If the formation of otic vesicles and fins turns out less abnormal than the addition of thalidomide alone, then the antagonist candidate is determined to be an antagonist.

(3) Mutated CRBN

The mutated CRBN of the present invention is characterized by having the following amino acid substitution (a) and/or (b).

(a) Substitution of tyrosine at position 384 from the N-terminus of human CRBN or an equivalent amino acid with alanine.

(b) Substitution of tryptophan at position 386 from the N-terminus of human CRBN or an equivalent amino acid with alanine.

In the present invention, "an amino acid equivalent to tyrosine at position 384 from the N-terminus of human CRBN" means, as shown in FIG. 12, an amino acid that matches tyrosine at position 384 from the N-terminus of human CRBN when aligned based on the amino acid identity. As shown in FIG. 12, in the mouse CRBN, tyrosine at position 361 from the N-terminus; in zebrafish CRBN, tyrosine at position 374 from the N-terminus; in *Drosophila melanogaster* CRBN, tyrosine at position 517 from the N-terminus; and in *Arabidopsis thaliana* CRBN, tyrosine at position 504 correspond to the aforementioned equivalent amino acid. Similarly, in the present invention, "an amino acid equivalent to tryptophan at position 386 from the N-terminus of human CRBN" means an amino acid that matches tryptophan at position 386 from the N-terminus of human CRBN when aligned based on the amino acid identity. As shown in FIG. 12, in the mouse-derived CRBN, tryptophan at position 363 from the N-terminus; in zebrafish-derived CRBN, tryptophan at position 376 from the N-terminus; in *Drosophila melanogaster*-derived CRBN, tryptophan at position 519 from the N-terminus; and in *Arabidopsis thaliana*-derived CRBN, tryptophan at position 506 correspond to the aforementioned equivalent amino acid.

Transfection and expression of a nucleic acid encoding mutated CRBN in animals can be performed by a routine method. For example, it can be performed by constructing an expression vector carrying DNA encoding mutated CRBN and transfecting it into fertilized eggs of animals and the like. The animal into which the nucleic acid is transfected is not particularly limited as long as it is non-human, and for example zebrafish, chickens, mice, and rabbits can be used.

The mutated CRBN of the present invention retains a ubiquitin ligase activity, but does not bind to thalidomide. Therefore, an animal in which a nucleic acid encoding this mutated CRBN is introduced and expressed will acquire resistance against to thalidomide-induced teratogenicity.

An animal in which a nucleic acid encoding mutated CRBN is transfected and expressed can be used for, for example, analysis of pharmacological actions other than teratogenicity. Rabbits and chickens in which mutated CRBN is transfected will acquire resistance to teratogenicity; therefore, if thalidomide and its derivatives exhibit pharmacological actions in those animals after administration, such pharmacological actions will be all independent of teratogenicity. Hence, these animals in which this mutated CRBN is transfected, are extremely useful for analysis of the actions exerted by thalidomide that are independent of the mechanism of teratogenicity.

EXAMPLES

Example 1

Bind Ability of Thalidomide with CRBN and DDB1

To purify thalidomide-binding proteins, the present inventors performed affinity purification using FG beads, which are magnetic particles (Cited Literature 9). FR259625, a thalidomide derivative in which a carboxyl group is added was covalently immobilized on the FG beads (FIG. 6), and mixed and incubated with human HeLa cell extracts. Subsequently, the beads were washed, and the binding proteins were selectively eluted with free thalidomide, and the eluate fractions were analyzed by SDS-PAGE and silver staining. As a result, two proteins of 127 kDa and 55 kDa were found to be specifically eluted (FIG. 1A, Lane 3). When free thalidomide was added to extracts prior to mixing with the beads, the yields of these proteins obtained by affinity purification were reduced significantly (FIG. 1A, Lane 4), suggesting that these proteins specifically bind to thalidomide. The 127 and 55 kDa proteins were analyzed by mass spectrometry and identified as DDB1 and CRBN, respectively (Table 1). Identities of these proteins were also confirmed by Western blotting (immunoblotting) (FIG. 1A), and further, these proteins were isolated similarly as thalidomide binding protein from extracts of various cell types (FIG. 7). To determine whether this interaction with thalidomide is direct, the present inventors purified recombinant proteins. CRBN-FLAG, but not DDB1-V5-His, bound to thalidomide-immobilized beads (FIG. 1B). This implies that DDB1 binds to thalidomide indirectly via CRBN. Namely, these results show that thalidomide directly binds to CRBN (FIG. 1C), while DDB1 binds to thalidomide through its interaction with CRBN.

Table 1

Example 2

Formation of an E3 Complex by CRBN, DDB1 and Cul4A

Human CRBN was originally reported as a candidate gene for autosomal recessive mild mental retardation (Cited Literature 11), and encodes a 442-amino acid protein. This protein is evolutionarily well conserved from plants to humans. Although CRBN was reported to bind to DDB1 in a recent proteomic analysis (Cited Literature 12), the functional interaction was unclear, and the biological functions of CRBN are largely unknown.

Figure 8:
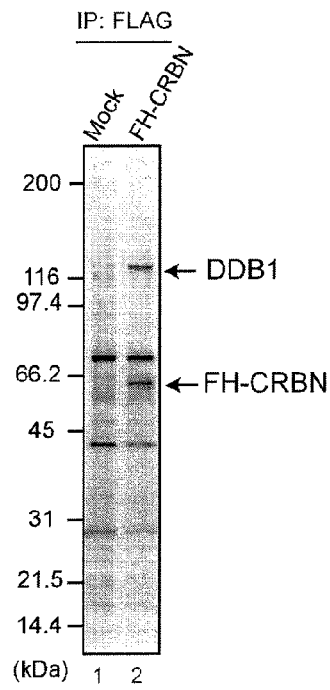
FIG. 8 relates to the bindability of DDB1 with CRBN. Extracts from a 293T cell line stably expressing FH-CRBN or control cells (mock) were immunoprecipitated with anti-FLAG antibody and subjected to SDS-PAGE and silver staining. As a result, DDB1 and CRBN were co-precipitated. DDB1 was coprecipitated with CRBN.

Initially, the present inventors carried out biochemical analysis to investigate the effects of thalidomide on CRBN functions. First, 293T cells stably expressing FH-CRBN was prepared, and extracts of the cells were subjected to immunoaffinity purification using anti-FLAG antibody to elucidate CRBN-binding proteins. Silver staining of the purified product revealed that CRBN binds to DDB1 at a mole ratio of nearly 1:1 (FIG. 8). Immunostaining (FIG. 2A) revealed that CRBN and DDB1 are colocalized mainly in the nucleus. This result suggests that they have crucial functions in the nucleus. DDB1 has been reported to be a component of E3 ubiquitin ligase complexes containing Cul 4 (Cul4A or Cul4B), a regulator of Cullin 1 (Roc1), and a substrate receptor (Cited Literatures 13 and 14). In principle, the function of E3 ubiquitin ligases is to direct the polyubiquitination of substrate protein by specifically interacting ubiquitin-conjugating enzyme (E2) (Cited Literatures 15 and 16). Cul4 serves as a scaffold protein, whereas Roc1 has a RING finger domain that associates with the E2 ubiquitin-conjugating enzyme. Substrate receptors, such as DDB2, CSA, SV5-V, CDT2, and AhR, directly bind to specific substrates and mediate their ubiquitination (Cited Literatures 13 and 7 to 20).

Figure 2:
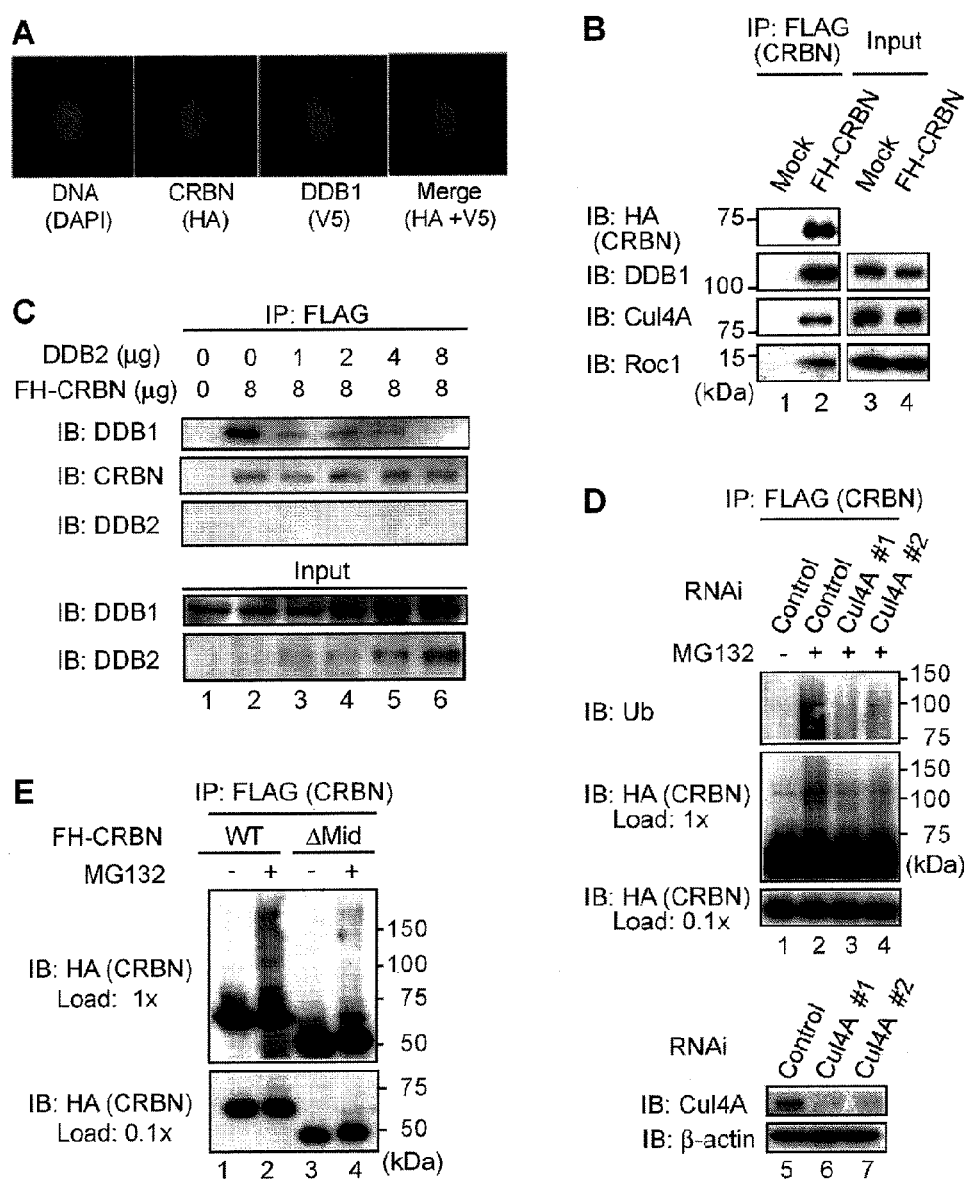
FIG. 2 relates to an E3 complex formation by CRBN, DDB1, and Cullin 4A (Cul4A). (A) FLAG and Hemagglutinin (HA)-epitope tagged (FH)—CRBN and DDB1-V5-His were coexpressed in HeLa cells and immunostained. DAPI stands for 4'6-diamidino-2-phenylindole. CRBN and DDB1 were colocalized mainly in the nucleus, but also in the cytoplasm. (B) The extracts from 293T cells stably expressing FH-CRBN or control cells (mock) were immunoprecipitated with anti-FLAG antibody, and then subjected to Western blotting. As a result, DDB1, Cul4A, and Roc1 were coprecipitated with FH-CRBN. (C) 293T cells were cotransfected with the indicated amount of FH-CRBN and DDB2 expression vectors. Input and FLAG-specific immunoprecipitated were detected by western blotting(IB). The amount of DDB1 coprecipitated with CRBN was reduced in the presence of increasing amounts of coexpressed DDB2. (D) 293T cells stably expressing FH-CRBN were transfected with Cul4A or control siRNA, and treated with MG132. The cells were lysed with RIPA buffer. Cell lysate was immunoprecipitated with anti-FLAG antibody and then subjected to Western blotting using anti-ubiquitin (Ub) antibody. Autoubiquitination of CRBN was detected in the presence of MG132 and its ubiquitination was abrogated by Cul4A siRNA. (E) 293T cells stably expressing FH-CRBN (WT, wild type) or CRBN mutant deficient in DDB1 binding (ΔMid, deletion of amino acids 187 to 260) were treated with MG132 and processed as in (D). Ubiquitination of ΔMid was reduced compared with wild type CRBN.

The present inventors examined whether CRBN interacts with other components of the E3 complex and found that DDB1, Cul4A, and Roc1 form a complex with FH-CRBN (FIG. 2B). If CRBN is a novel substrate receptor, it would be expected to compete for binding to DDB1 with other substrate receptors subunits such as DDB2. In fact, the amount of DDB1 coprecipitated with CRBN was reduced in the presence of increasing amounts of coexpressed DDB2 (FIG. 2C). That is, the results indicate that CRBN functions as a substrate-binding subunit of a DDB1-Cul4-Roc1 E3 ubiquitin ligase complex.

Figure 9:
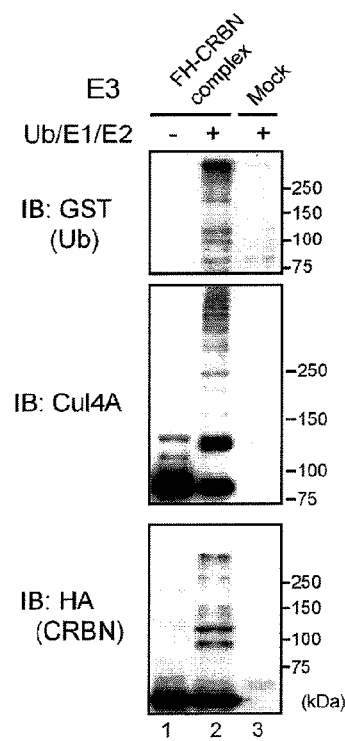
FIG. 9 relates to ubiquitination of CRBN in vitro. The FH-CRBN complex purified from 293T cells stably expressing FH-CRBN was incubated with or without GST-ubiquitin, Ubal (corresponding to E1), UbCH5b (corresponding to E2) and ATP, and aliquots of the reactions were detected by western blotting with the indicated antibodies. Mock is purified from control cells. Autoubiquitination was observed in the presence of the CRBN complex.
Figure 10:
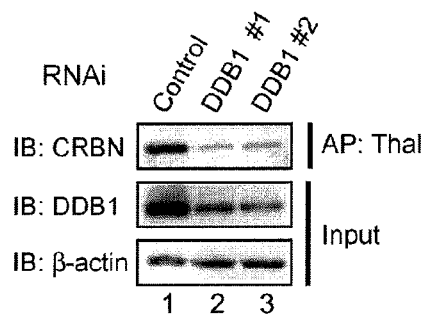
FIG. 10 shows the relationship between DDB1 knockdown and CRBN protein levels. 293T cells were transfected with DDB1 or control siRNA, and the resulting lysates were mixed with thalidomide-immobilized beads. In put or bound protein were analyzed by western blotting using anti-DDB1 or CRBN antibody. Knockdown of DDB1 leads to a substantial reduction of the CRBN protein levels.

The present inventors examined whether the CRBN complex actually has an E3 ubiquitin ligase activity. Substrate receptors and Cul4 are known to undergo autoubiquitination in vitro. As a result of an in vitro ubiquitination assay using GST-tagged ubiquitin, Una1 (E1), Uba12 (E2), and the CRBN complex, ubiquitination activity was indeed observed in the presence of CRBN complex (FIG. 9). In order to examine whether CRBN is autoubiquitinated in living cells, 293T cells expressing FH-CRRBN were treated with proteasome inhibitor MG132. It was found that autoubiquitination of CRBN was detected in the presence of MG132, and its ubiquitination was reduced by siRNA-mediated suppression of Cul4A expression (FIG. 2D). Knockdown of DDB1 led to a substantial reduction of CRBN protein level (FIG. 10), it was not possible to determine the effect of suppression of DDB1 expression on CRBN autoubiquitination. Nevertheless, this finding suggests that DDB1 and CRBN are functionally linked.

Figure 11:
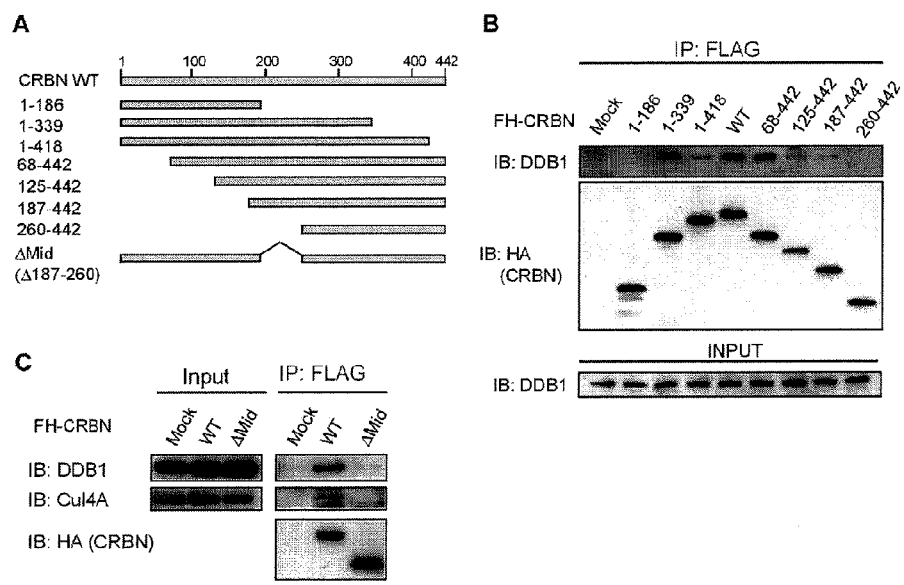

In order to elucidate the role of DDB1 in the CRBN function, the present inventors prepared a CRBN mutant deficient in DDB1 binding. Deletion mutation analysis revealed that a deletion of amino acids 187 to 260 of CRBN abolishes its interaction with DDB1 (FIG. 11, ΔMid). Autoubiquitination in ΔMid-expressing 293T cells treated with MG132 was found to be markedly reduced compared to 293T cells in which wild-type CRBN was expressed. Based on the above results, it was suggested that CRBN is a subunit of a functional E3 ubiquitin ligase complex and undergoes autoubiquitination in a Cul4A and DDB1-dependent manner.

Example 3

Inhibition of CRBN Function by Thalidomide

Figure 3:
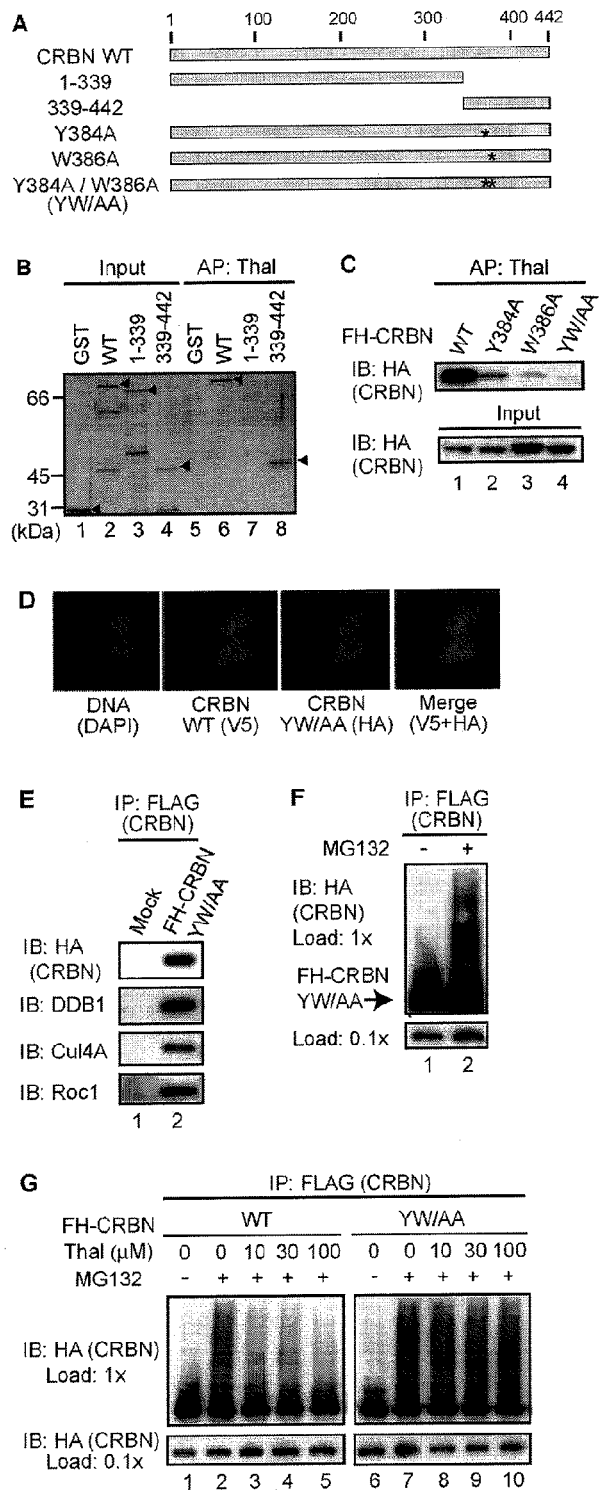
FIG. 3 relates to the inhibition of CRBN function by thalidomide. (A) Schematic representation of CRBN and its deletion mutant. Asterisks indicate the positions of alanine substitutions. (B) GST-CRBN wild type or mutant protein was mixed with thalidomide-immobilized beads, and the bound CRBN mutants were stained with silver staining. The wild type CRBN and mutant protein expressing the C-terminal 104 amino acid residues of CRBN were bound. The position of full-length GST-fusion proteins are indicated by arrowheads. (C) Extracts prepared from 293T cells overexpressing the FH-CRBN or its mutants were mixed with thalidomide-immobilized beads, and the bound CRBN mutants were detected by Western blotting. Two position mutants, CRBN Y384A and W386A were defective for thalidomide binding. Moreover double mutant CRBN YW/AA had extremely low thalidomide binding activity. (D) CRBN-V5-His (wild type) and its mutant FH-CRBN YW/AA were cotransfected in Hela cells and immunostained. DAPI indicates 4'6-diamidino-2-pheynylindole. The subcellular localization of mutant was indistinguishable from wild type CRBN (E) 293T cells expressing FH-CRBN YW/AA were immunoprecipitated with anti-FLAG antibody and western blotted. CRBN YW/AA was coprecipitated with DDB1, Cul4A and Roc1. (F and G) 293T cells stably expressing FH-CRBN (wild type) or FH-CRBN YW/AA were processed as in FIG. 2E. In (G), cells were treated with indicated concentration of thalidomide for 4 hours before harvesting. Autoubiquitination of CRBN by MG132 was suppressed by pretreatment with thalidomide, whereas autoubiquitination of CRBN YW/AA was not affected by thalidomide.

In order to elucidate the molecular basis of the CRBN-thalidomide interaction and its functional significance, the present inventors attempted to obtain a CRBN point mutant that does not bind to thalidomide, but is assembled into a functional E3 complex. First, thalidomide-binding region was investigated by using the N-terminal and C-terminal deletion mutants. As a result, it was revealed that the thalidomide-binding region was the C-terminal 104 amino acids (FIGS. 3A and B). Homology analysis of numerous CRBN homologs from *Arabidopsis thaliana* to humans showed that the C-terminal region was highly conserved (FIG. 12). Assuming that evolutionarily well conserved residue may be important for thalidomide binding, several point mutants were constructed, and two point mutants, Y384A and W386A, were found to be defective for thalidomide binding (FIG. 3C). Moreover, Y384A/W386A (a mutant called CRBN YW/AA, in which two residues were simultaneously substituted) was found to have an extremely low thalidomide-binding activity (FIG. 3C). The present inventors investigated whether this CRBN YW/AA functionally active in the cells. The subcellular localization of this mutant was indistinguishable from that of wild-type CRBN. The present inventors found that CRBN YW/AA was coprecipitated with DDB1, Cul4A and Roc1 and was autoubiquitinated in the presence of MG132 (FIGS. 3E and F). That is, it was revealed that CRBN YW/AA formed an E3 complex similarly to wild-type CRBN, and also retaining the function.

The present inventors examined whether thalidomide would inhibit ubiquitination of the CRBN-containing E3 complex. 293T cells stably expressing FH-CRBN or FH-CRBN YW/AA were treated with MG132 and thalidomide (10, 30, and 100 μM) at similar concentration relative to the therapeutic doses used in human. Autoubiquitination of wild-type CRBN was potently inhibited by thalidomide, whereas autoubiquitination of CRBN YW/AA was not affected by thalidomide (FIG. 3G). These results suggest that thalidomide inhibits the E3 function by binding to CRBN.

Example 4

CRBN as an In Vivo Target of Thalidomide

Next, the present inventors examined the role of CRBN in the thalidomide-induced teratogenicity in an animal model. Thalidomide is teratogenic in rabbits and chickens, but not in mice (Cited Literatures 1 to 3). In this study, the present inventors used zebrafish (*Danio rerio*) as a model for the following reasons: (i) the rapid progress of development can be monitored in real time because of the transparency of the embryo, (ii) genetic suppression can be carried out easily (Cited Literature 21), and (iii) zebrafish is suitable for pharmaco-toxicological studies (Cited Literature 22). Although it had been unknown if thalidomide would exhibit teratogenicity also in zebrafish, thalidomide has recently been shown to inhibit angiogenesis in zebrafish (Cited Literature 23), and therefore the present inventors reasoned that thalidomide would also exhibit teratogenicity in zebrafish.

Figure 4:
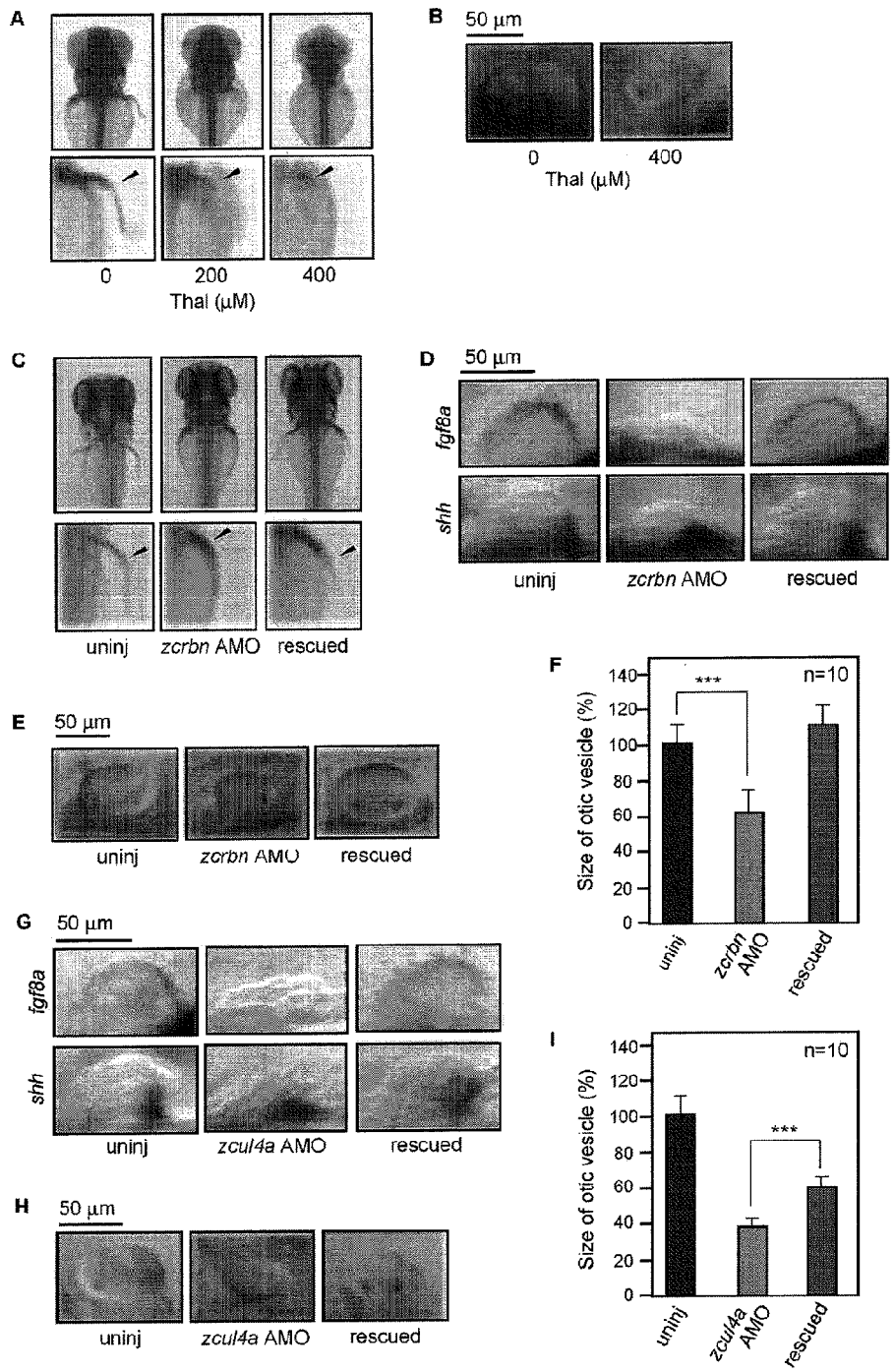
FIG. 4 relates to developmental defects in zebrafish and suppression of a CRBN complex by thalidomide treatment. (A and B) Zebrafish embryos were allowed to develop in media containing the indicated concentration of thalidomide. In thalidomide-treated embryos, the development of pectoral fin and otic vesicles was disturbed. (C to F) zcrbn antisense morpholino oligonucleotide (zcrbn AMO) was injected with or without zcrbn mRNA into one cell stage embryos. Embryos injected with zcrbn AMO exhibited specific defects in fin and otic vesicle development, these phenotypes were rescued by coinjection of zcrbn mRNA. (G to I) Where indicated, zcul4a AMO was injected with or without zcul4a mRNA into one cell stage embryos. Injection of zcul4a AMO caused similar defects in otic vesicles and pectoral fin, and these phenotypes were rescued by coinjection of zcul4a mRNA. (A and C) Embryos at 75 hpf were fixed and stained with Alcian blue. Upper panels show dorsal view of embryos, and lower panels show close-up view of pectoral fins. Pectoral fins are indicated by arrowheads. (B, E, and H) Close-up view of otic vesicles at 30 hpf embryos. (D and G) Embryos at 48 hpf were subjected to hybridization with antisense probe for fibroblast growth factor 8a (fgf8a) and sonic hedgehog (shh). Close-up view of fin bud. Knockdown of zcrbn or zcul4a resulted in a reduction of fgf8a expression, and these phenotypes were rescued by coinjection of zcrbn or zcul4a mRNA, respectively. It had little effect on shh expression. (F and I) The size of the otic vesicles at 30 hpf is shown in the graphs in comparison to an untreated sample. (***$p<0.001$, uninj, uninjected or untreated).
Figure 5:
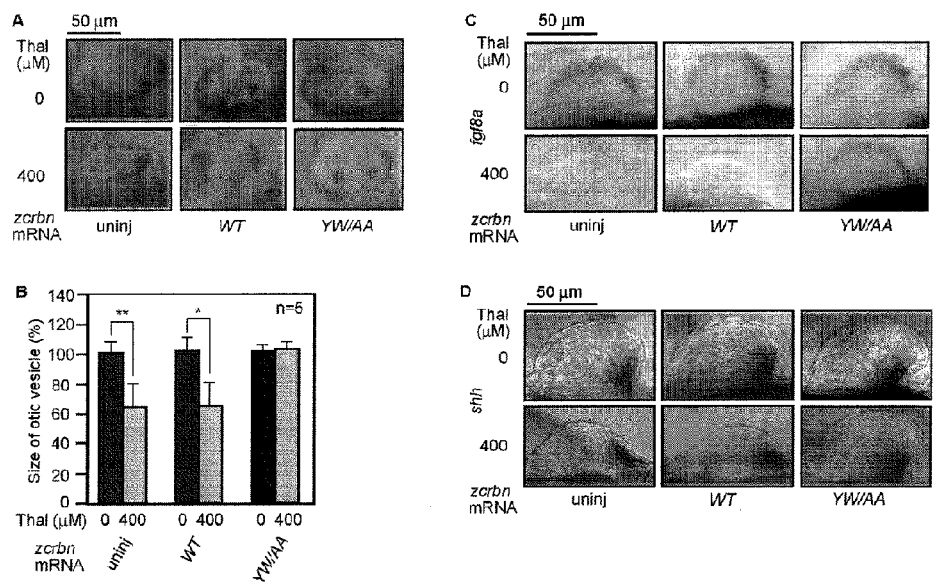
FIG. 5 shows the reduction of the thalidomide-induced teratogenicity by expression of mutated CRBN. zcrbn mRNA (wild type) or zcrbn YW/AA mRNA were injected in one-cell stage embryos. Embryos were allowed to develop in the presence or absence of thalidomide. (A) Close-up view of otic vesicles at 27 hpf are shown. (B) Otic vesicle size of 30 hpf embryos relative to the size of embryos. *p<0.05, **p<0.01. Thalidomide treatment of embryos overexpressing zcrbn YW/AA did not affect otic vesicle size. (C and D) Embryos at 48 hpf were subjected to in situ hybridization with antisence probes for fgf8 or shh. Figures show close-up image of fin buds. uninj, uninjected. In thalidomide-treated embryos, fgf8a expression was severely reduced, whereas fgf8a expression was restored by injection of zcrbn YW/AA mRNA.

To elucidate possible effects of thalidomide on zebrafish development, dechorionated embryos were transferred to media containing various concentrations of thalidomide. Thalidomide was added two hours post fertilization (hpf) and the developmental process was observed for three days. It was revealed that in thalidomide-treated embryos, development of pectoral fins and otic vesicles was disturbed (FIGS. 4A and B), whereas other aspects of development were not affected. More specifically, formation of the endoskeletal disc of the pectoral fin was inhibited at 75 hpf (FIG. 4A), and the size of otic vesicles at 30 hpf was reduced (FIG. 4B). Retardation of pectoral fin development was also detected at 48-hpf embryos (FIGS. 5C and D). Recent studies have reported that development of pectoral fins and otic vesicles in teleosts (including zebrafish) shares common molecular mechanisms with the limb and ear development in tetrapods (Cited Literatures 24 to 26). Thus, the thalidomide-induced developmental defects in zebrafish are quite similar to the developmental defects in women administered with thalidomide during the initial period of pregnancy, suggesting that the thalidomide-induced teratogenicity is conserved across vertebrate species.

Figure 13:
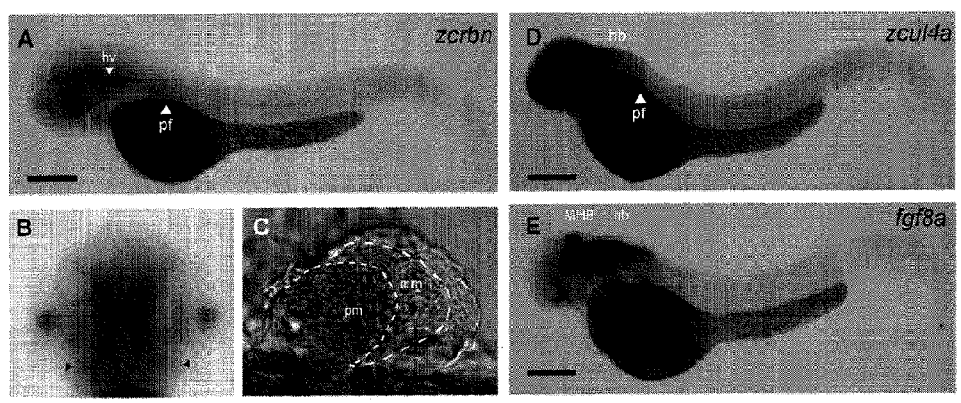
FIG. 13 shows the expression of zcrbn and zcul4a in zebrafish embryos. The expression of zcrbn and zcul4a in 48 hpf embryos was examined by whole-mount in situ hybridization. (A) zcrbn is highly expressed at head vasculature, pectoral fins and brain. Lateral view. (B) zcrbn expression at otic vesicles (OV, arrowheads) at 48 hpf. Dorsal view. (C) A close-up view of zcrbn expression at pectoral fins at 48 hpf embryos. Expression is seen at high levels at proximal mesenchyme (pm) and weakly in migratory mesenchyme (mm). (D) zcul4a is expressed abundantly at forebrain, midbrain, hindbrain, and pectoral fins at 48 hpf. (E) Expression of fgf8 in 48 hpf embryos was examined as a control. fgf8 is expressed at mid-hindbrain boundary and hindbrain. Scale bars, 0.2 mm.
Figure 14:
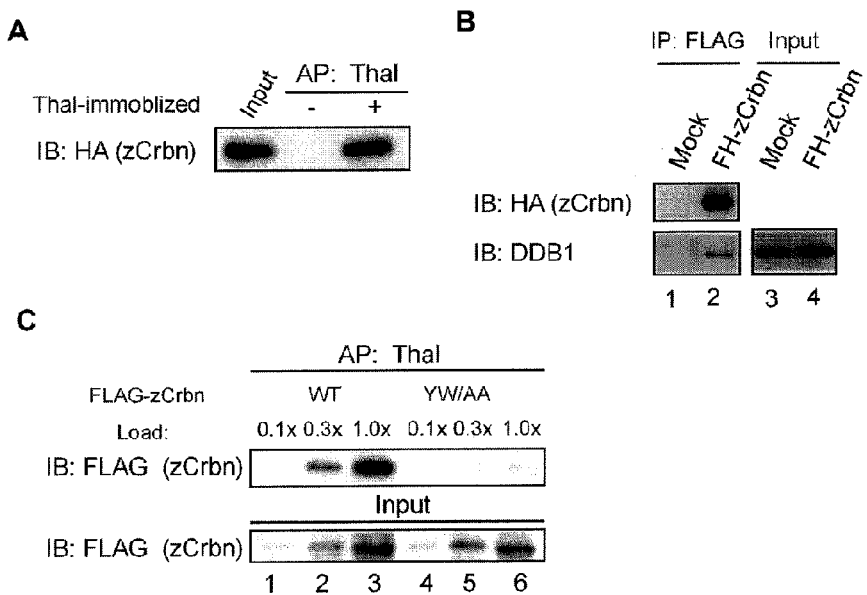
FIG. 14 relates to biochemical analysis results of zCrbn. (A) Extract of 293T cells stably expressing FH-zCrbn was mixed and incubated with thalidomide beads. Bound proteins were eluted by thalidomide, and eluate were analyzed by western blotting. zCrbn bound to thalidomide. (B) Lysate from 293T cells overexpressing FH-zCrbn was immunoprecipitated with anti-FLAG antibody, and DDB1 was detected by western blotting. It was revealed that human endogenous DDB1 bound to FH-zCrbn. (C) Lysate from FLAG-zCrbn (wild type) or FLAG-zCrbn YW/AA overexpressed in 293T cells was mixed with thalidomide beads. For quantification, various amounts of input and eluate fraction were analyzed by western blotting. Binding of thalidomide to zCrbn YW/AA was obviously weak.

Zebrafish also have a CRBN ortholog (homologous gene found in different species), which will be called zcrbn. The gene product of zcrbn has approximately 70% identity to human CRBN. The present inventors first analyzed the expression pattern of zcrbn mRNA and found that the gene was expressed in brain, head vasculature, ear and pectoral fin at 48 hpf (FIG. 13). It was shown that zCrbn bound to both thalidomide and human DDB1 (FIG. 14), suggesting that the results of the human cell line are also valid in zebrafish. Next, the function of zCrbn during the early development of zebrafish was analyzed. Consistent with the effects of thalidomide, embryos injected with antisense morpholino oligo (AMO) for zcrbn exhibited defects in the fin and otic vesicle development (FIGS. 4C to F), with phenotypes similar to those of thalidomide-treated embryos. In zcrbn-AMO injected embryos at 27 hpf, for example, the size of otic vesicles was reduced by as much as 40% compared to that of wild type (FIG. 4F). These defects were rescued by coinjection of zcrbn mRNA (FIGS. 4C to F).

The above results suggested a highly possibility that thalidomide exerts teratogenic actions by inhibiting the zCrbn function. If so, its teratogenicity should be alleviated by expression of functionally active but thalidomide-binding-defective zCrbn. To examine this idea, the present inventors prepared mutants in which Y374 and W376 are substituted with alanine (corresponding to YW/AA in humans, namely Y384A/W386A). The zCrbn YW/AA has extremely low thalidomide-binding activity. In the absence of thalidomide, Overexpression of wild-type zCrbn or zCrbn YW/AA had no discernible effect on fin and otic vesicle development. As shown in FIG. 4B, treatment with 400 µM thalidomide significantly reduced the size of otic vesicles (64.5% of the control size, FIGS. 5A and B). Also thalidomide treatment of embryos overexpressing wild-type zCrbn reduced the size of otic vesicles to approximately 66% of the control size. Importantly, however, thalidomide treatment of embryos overexpressing zCrbn YW/AA did not affect the size of otic vesicles (p=0.347). Thalidomide-induced fin degeneration was also rescued by overexpression of zCrbn YW/AA. These results demonstrate that thalidomide has exerted teratogenicity by binding to CRBN and inhibiting its function.

Example 5

Molecular Mechanism of the Thalidomide-Induced Teratogenicity

As the connection between thalidomide and CRBN was revealed, the present inventors examined whether the CRBN-containing ubiquitin ligase complex is involved in the thalidomide-induced teratogenicity, by suppression of zCul4A expression. The zcul4a mRNA is abundantly expressed in brain and fin (FIG. 13). As expected, zcul4a AMO caused defects in otic vesicles and fins (FIGS. 4G to I). The size of otic vesicles was markedly reduced in zCul4a knockdown embryos at 27 hpf (40% of the control size), which was partially rescued by coinjection of zcul4a mRNA. Incomplete rescue may be due to excessive potency of zcul4a AMO. Nevertheless, these results suggested that the ubiquitin ligase complex is necessary for the ear and fin development, and is a target of thalidomide.

The above results revealed that ubiquitination of certain proteins by the CRBN-containing E3 complex is important for the ear and fin development, and suggested that thalidomide-induced developmental defects are associated with the CRBN-containing E3 complex malfunction. To obtain a clue to the pathway(s) downstream of CRBN and thalidomide, the present inventors analyzed well-known key molecules in fin development. Sonic hedgehog (Shh) is expressed in the zone of polarizing activity (ZPA) and is responsible for anteroposterior patterning of the limb and fin (Cited Literature 27), whereas Fgf8 is expressed in the apical ectodermal ridge (AER) of the limb and fin and is necessary for outgrowth of the limb and fin along the proximodistal axis. In thalidomide-treated 48-hpf embryos, fgf8a expression was reduced or absent (FIG. 5C), whereas no change was observed in shh expression (FIG. 5D). In addition, reduction in the fgf8a expression by thalidomide was restored by concomitant injection of zCrbn YW/AA. expression of fgf8a was also reduced in zCrbn or zCul4a AMO injected embryos, whereas there was no difference in shh expression. Thus, an inhibitor of FGF8 production is a possible downstream target of thalidomide and the CRBN-containing E3 complex.

Example 6

Bindability of Phthalimide with CRBN and DDB1

The bindability of phthalimide, which is a known non-teratogenic thalidomide derivative, with CRBN and DDB1, was investigated as follows.

Figure 16:
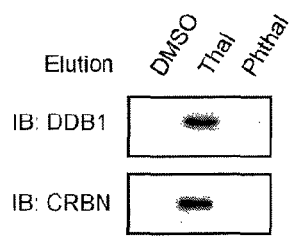
FIG. 16 shows the binding of phthalimide to CRBN and DDB1. Extracts of 293T cells were mixed with thalidomide-immobilized beads. Bound proteins were eluted with thalidomide or an equal amount of phthalimide, and eluate fractions were analyzed by western blotting.

Thalidomide-immobilized beads were mixed with Extracts of 293T cells and then washed. Thalidomide-bound factors were eluted from the beads by thalidomide or phthalimide. CRBN and DDB1 in the eluate fractions were analyzed by Western blotting. Although CRBN and DDB1 were detected in the thalidomide eluate fraction, these proteins were not detected in the phthalimide (Phthal) eluate fraction (FIG. 16).

Example 7

Study on Binding of Thalidomide Derivatives to CRBN

Figure 17:
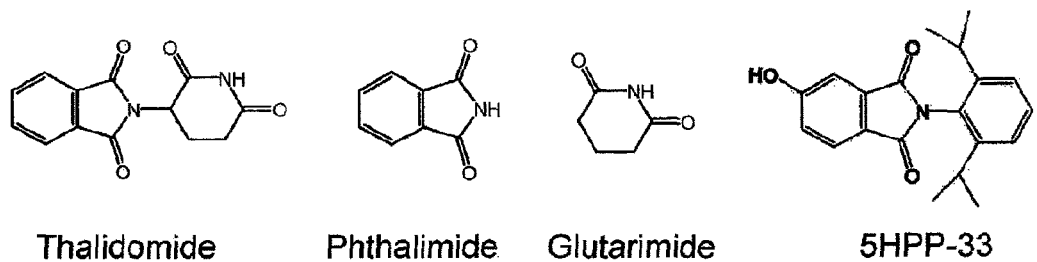
FIG. 17 shows the structural formulas of the thalidomide derivatives whose binding affinity to CRBN was examined.
Figure 18:
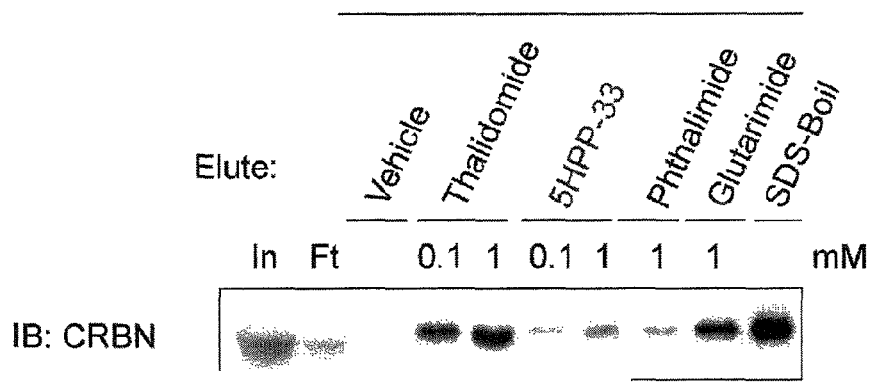
FIG. 18 shows the binding of the thalidomide derivatives to CRBN. Extracts of 293T cells were mixed with thalidomide-immobilized beads. Bound proteins were eluted with thalidomide derivatives. After washing, bound proteins were eluted by thalidomide derivatives. Eluate fraction were analyzed by western blotting. The "Vehicle" in the Figure indicates DMSO. SDS-Boil indicates a fraction in which bound proteins were detached by heating the beads at 98.5° C. in buffer containing 2% SDS. CRBN was eluted with thalidomide and glutarimide, but not eluted with phthalimide and 5-hydroxy-(2,6-diisopropylphenyl)-1H-isoindole-1,3-dione (5HPP-33).

Extracts of 293T cells were mixed and incubated with thalidomide-immobilized beads for two hours. Subsequently, the beads were washed three times with a 0.5% NP-40 lysis buffer (Tris-HCl, pH 8, 150 mM NaCl, 0.5% NP-40), and mixed with a 0.5% NP-40 lysis buffer containing 0.1 to 1 mM thalidomide, phthalimide, glutarimide or 5HPP-33 (structural formulas of respective compounds are shown in FIG. 17) for one hour to elute CRBN. The eluate fractions were analyzed by SDS-PAGE and Western blotting using an antibody against CRBN. The results are shown in FIG. 18.

As shown in Figure, very little CRBN was eluted by buffer containing phthalimide or 5HPP-33. From this result, phthalimide and 5HPP-33 are considered to have low bindability with CRBN.

Example 8

Growth Inhibition of Multiple Myeloma Cells

Inhibitory actions of thalidomide and 5HPP-33 on proliferation of the multiple myeloma cell Kms12 were investigated.

Figure 19:
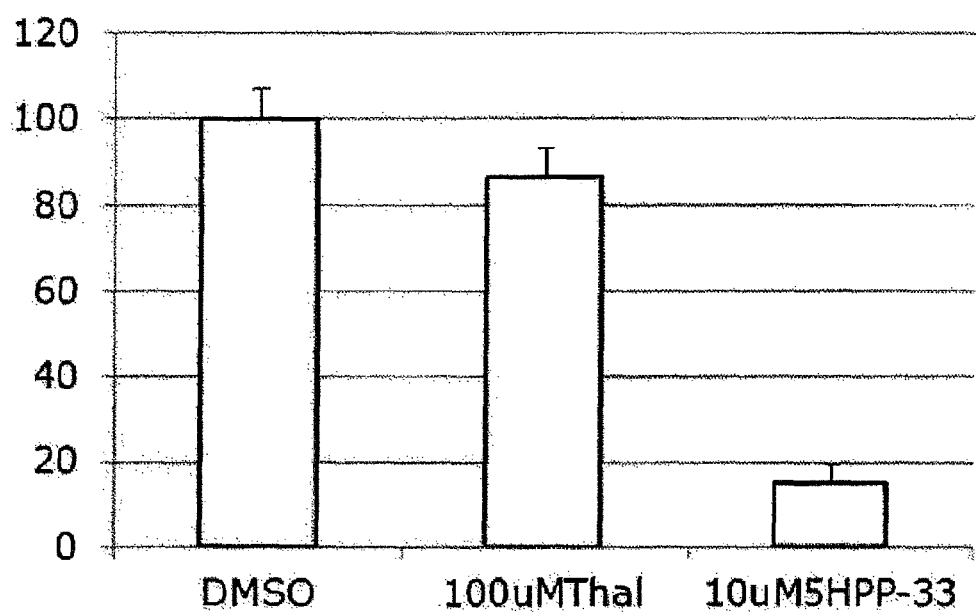
FIG. 19 shows the number of the multiple myeloma cell Kms12 after treatment with thalidomide and 5HPP-33. KMS-12 cells were incubated with thalidomide or 5HPP-33 (100 μM) for 48 hours at 37° C. in 5% $CO_2$. For measurement of the number of the living cells, Cell Count-Reagent SF (Nacalai Tesque, Inc.) was added to culture media for 2 hours at the end of the 48 hours culture. The absorbance at 450 nm was measured. It was shown that 5HPP-33 potently suppressed myeloma cell growth.

Multiple myeloma cell Kms12 were cultured in RPMI Medium 1640 containing 10% FBS. For treatment with drugs, the medium was adjusted to contain $2\times10^5$ Kms12 cells/ml and dispensed in 2 ml Eppendorf tubes in 2 ml aliquots. As the stock solution, thalidomide or 5HPP-33 were dissolved in dimethylsulfoxide (DMSO) at concentration of 100 mM and 10 mM respectively. The stock solution was added to the cell suspension at 2 µl/2 ml, followed by gentle and thorough inversion mixing. Cell mixture was dispensed in a 96 well plate at 100 µl/well and cultured at 37° C. and 5% $CO_2$ for 48 hours. For measurement of the number of the living cells, Cell Count-Reagent SF (Nacalai Tesque, Inc.) was added to culture media and incubated for 2 hours. The absorbance at 450 nm, which is correlate to the number, were measured by GloMax-Multi+ Detection System (Promega KK) For preparation of a calibration curve, $1\times10^6$, $3\times10^5$ and $1\times10^5$ Kms12 cells/ml were used. Defining the number of cells treated with the solvent as 100, the number of cells treated with the drugs were expressed as relative values. The relative values of cell numbers are shown in FIG. 19.

As shown in Figure, 5HPP-33 exhibited a potent suppressive action on proliferation of the multiple myeloma cell Kms12. As shown in Example 7, the bindability of 5HPP-33 with CRBN is low. Accordingly, the growth inhibitory action of 5HPP-33 is considered to be irrelevant to binding to CRBN.

[Discussion]

The idea that CRBN functions as a substrate receptor subunit of a DDB1-Cul4A-Roc1 E3 ubiquitin ligase complex is supported by the following results. First, the binding of CRBN to DDB1 was competitive with DDB1, a well known substrate receptor. Second, CRBN undergoes autoubiquitination as do other substrate receptors. Although many substrate receptors, including DDB2, possess a WDXR motif (Cited Literatures 11 and 19), whereas a few substrate receptors are known to lack this motif (Cited Literatures 13 and 18). As CRBN does not have an identifiable WDXR motif, this protein might be a substrate receptor of the latter type. As additional results for the above idea, it was shown that suppression of CRBN and Cul4A expression caused similar developmental defects in zebrafish. However, suppression of Cul4A expression resulted in a more severe phenotype than suppression of CRBN expression. This observation is not surprising since CRBN is only one of several substrate receptors associated with the DDB1-Cul4-Roc1 complex, and so only these complexes would be affected by CRBN, while all DDB1-Cul4 ubiquitin ligase complexes would be affected by suppression of Cul4A expression.

The mechanism of action of thalidomide is multifaceted, but is not fully understood. The immunomodulatory and anti-angiogenic actions of thalidomide have been proposed to be partly responsible for its teratogenic activity, as well as its therapeutic value in the treatment of erythema nodosum leprosum and multiple myeloma (Cited Literatures 2 and 3). Also, thalidomide has been reported to suppress the production of some cytokines such as TNF-alpha and VEGF (Cited Literatures 30 and 31). Thalidomide is also capable of inducing apoptosis and production of reactive oxygen species (ROS) (Cited Literatures 3, 4, and 32). Despite accumulation of these data, the direct target of thalidomide had remained unknown. Here, the present inventors obtained several lines of evidence that CRBN is a primary target of the thalidomide-induced teratogenicity. First, thalidomide directly binds to CRBN to inhibit autoubiquitination of CRBN. This is caused by inhibition of the formed ubiquitin ligase containing CRBN, and similar phenomena are reported also in other ubiquitin ligases (Cited Literature 33). Second, thalidomide-induced developmental defects in zebrafish are similar to those of CRBN knockdown, and it is alleviated by overexpression of the CRBN mutant that does not bind to thalidomide. Third, FGF8, which is essential for limb and fin outgrowth, is a downstream target of thalidomide and the CRBN complex (FIGS. 4D, 4G, and 5C). These results are consistent with the previous reports, in which suppression of fgf8 expression by thalidomide has already been demonstrated in an experiment using rabbits (Cited Literature 34). Also, it is reported that in developing chick limb buds, thalidomide upregulates the expression of bone morphogenetic protein (BMP) and induce apoptosis (Cited Literature 32). Further, mouse BMPs have been reported to suppress FGF8 expression and induce apoptosis in the AER (Cited Literature 35). That is, CRBN is a missing link between thalidomide and these developmental regulators.

Figure 15:
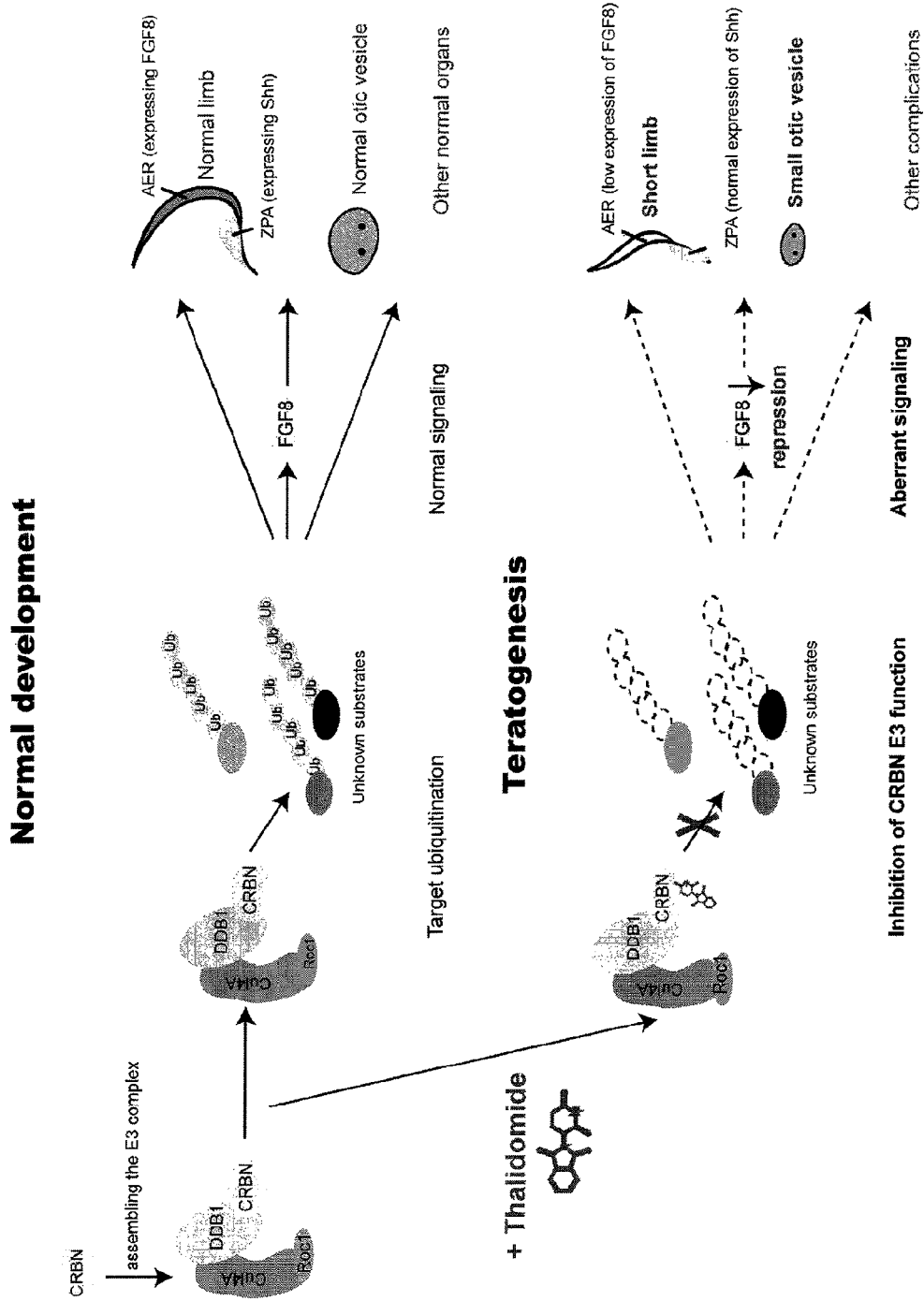
FIG. 15 illustrates the schematic model for the molecular mechanism of thalidomide teratogenicity. Normally, CRBN functions as a component of the E3 ubiquitin ligase to regulate multiple developmental processes, such as limb and otic vesicle formation, by ubiquitinating unknown substrates (top diagram). Thalidomide binds to CRBN and inhibits the associated E3 function (bottom diagram). Aberrant accumulation of its substrate(s) causes multiple developmental defects, such as short limbs and small otic vesicles, in part through downregulation of fgf8 expression.

The aforementioned results of Examples suggest that thalidomide exerts its teratogenicity by binding to CRBN and inhibiting the associated ubiquitin ligase activity (FIG. 15). The present inventors speculate that regulation of ubiquitin-dependent proteolysis by thalidomide and CRBN leads to abnormal regulation of the BMP and FGF8 pathways and of developmental programs that require their normal functions. Other developmental factors may be affected as well. There are, however, a number of unanswered questions, such as: what are target substrates of the CRBN E3 ubiquitin ligase?; how does thalidomide inhibit the ubiquitination of CRBN? These issues need to be addressed.

[Experimental Method and Materials]
(1) Reagents

Thalidomide (Tocris Cookson) was dissolved in dimethyl sulfoxide (DMSO) at a final concentration of 400 mM by heating at 65° C. and used immediately. MG132 was dissolved in DMSO at a final concentration of 10 mM. The same amounts of DMSO were used as control in the experiments.

(2) Preparation of Thalidomide-Immobilized Beads

Figure 6:
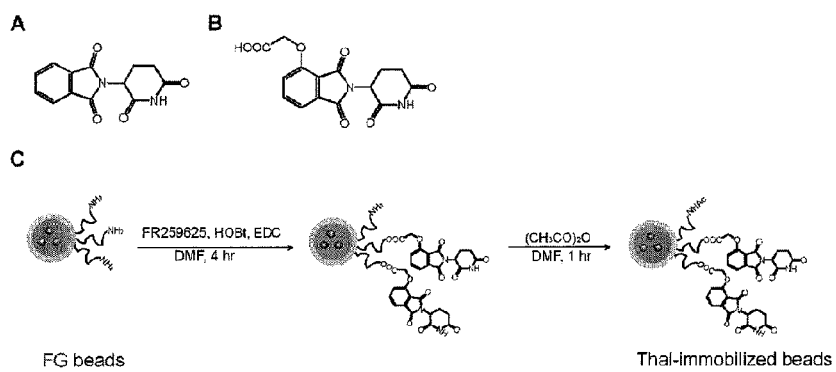
FIG. 6 Scheme of thalidomide immobilization to FG beads (A and B) Structures of thalidomide and its derivative, FR259625. (C) Scheme of thalidomide immobilization to FG beads is shown.
Figure 7:
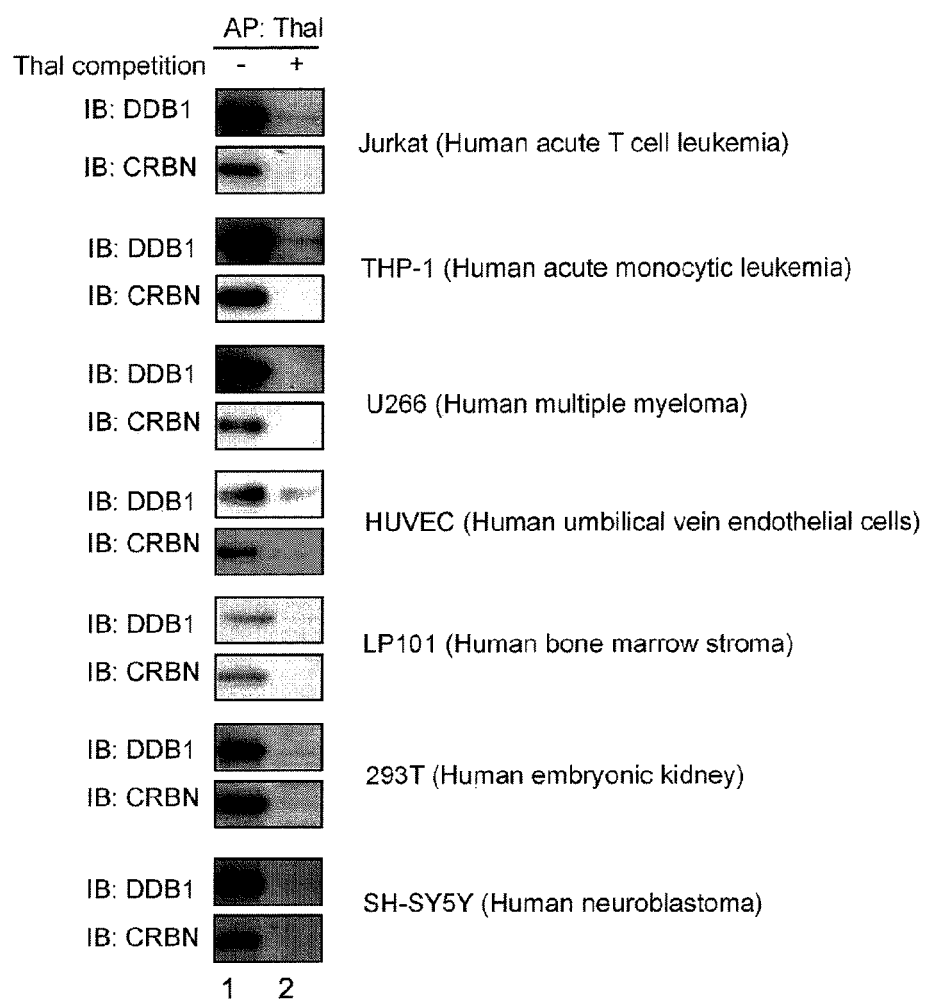
FIG. 7 relates to purification of thalidomide-binding factors from various cell types. Extracts prepared from the indicated cell lines were subjected to affinity purification with thalidomide-immobilized beads. Elute fractions were analyzed by western blotting using anti-DDB1 and anti-CRBN antibody. Where indicated, 0.3 mM thalidomide was added to extracts prior to incubation with the beads. CRBN and DDB1 were isolated as thalidomide-binding proteins from various cell types.

A diagram regarding the preparation of thalidomide-immobilized beads is shown in FIG. 6. Magnetic FG beads (5 mg, Cited Literature 10) were reacted with 10 mM 1-hydroxybenzotriazole, 10 mM 1-ethyl-3-(3-dimethylaminepropyl)-carbodiimide HCl, and 2 mM FR259625 (carboxyl thalidomide derivative) in an N,N-dimethylformamide (DMF) solvent for four hours at room temperature. Unreacted residues in FG beads were masked using 20% carbonic anhydride in DMF, and the resulting beads were stored at 4° C.

(3) Affinity Purification with Thalidomide-Immobilized Beads

Thalidomide-immobilized beads (0.5 mg) were equilibrated with a 0.5% NP-40 lysis buffer (50 mM Tris HCl, pH 8, 150 mM NaCl, 0.5% NP-40). Cell extracts were prepared from HeLa, Jutkat, THP-1, U266, HUVEC, LP101, SH-SY5Y, and 293T cells as described in a literature (Cited Literature 36). The extracts were mixed with the beads and incubated for two hours. The beads were washed three times with a 0.5% NP-40 lysis buffer, and the bound proteins were eluted with 1 mM thalidomide. In some experiments, 0.3 mM thalidomide was added to extracts before mixing with the beads. To examine whether or not phthalimide has bindability, 1 mM phthalimide was used in place of 1 mM free thalidomide in the process of elution.

(4) Plasmids

CRBN and DDB2 cDNAs were obtained by RT-PCR from HeLa total RNA. The CRBN mutants were generated by standard PCR techniques. DDB1 cDNA was provided by Dr. Matsunaga. The zCrbn and zCul4a cDNAs were obtained by RT-PCR from 24-hpf zebrafish total RNA. The following vectors were used in this study: pcDNA3.1-FH-N, pcDNA6/V5-His (Invitrogen), pFastBac1 (Invitrogen), pLenti6 (Invitrogen), pFASTBAC1 (Invitrogen), pLenti6 (Invitrogen), pCS2 (+) and pGEX6P-1 (GE Healthcare). The pcDNA3.1-FH-N is a derivative of pcDNA3.1 containing a frgment encoding FLAG-HA sequence.

(5) Antibodies

Anti-CRBN antibody were generated in rabbit against CRBN (65-76). Antibody against FLAG (M2, Sigma), HA (3F10, Roche), V5 (V5-10, Sigma), GST (Sigma), DDB1 (Abeam), and Roc1 (Zymed) were obtained from commercial sources. Anti-Cul4A and anti-DDB2 antibodies were kindly provided by Dr. Raychaudhuri and Dr. Matsunaga, respectively.

(6) In Vitro Binding Assay Using Thalidomide-Immobilized Beads

Recombinant CRBN-FLAG and DDB1-V5-His proteins were expressed in the insect Sf9 cells by using the Bac-to-bac baculovirus expression system (Invitrogen) and purified using anti-FLAG M2 agarose beads (Sigma) and Ni-NTA agarose beads (Qiagen), respectively. Purified CRBN-FLAG and/or DDB1-V5-His were mixed with thalidomide-immobilized beads, and the bound proteins were eluted with an SDS sample buffer. For analysis of CRBN-deletion mutant, GST-fused CRBN and its mutants were expressed in E. coli BL21 and purified using glutathione Sepharose (GE Healthcare). CRBN mutants were overexpressed in 293T cells by transfection using Lipofectamine 2000 (Invitrogen). Subsequent binding assays were carried out as described above.

(7) Coimmunoprecipitation

To analyze interactions between CRBN and DDB1, CRBN-FLAG and DDB1-V5-His were coexpressed in Sf9 cells. Cell extracts were mixed with Anti-FLAG agarose beads, and the bound proteins were selectively eluted with FLAG peptide. To purify the CRBN complex, 293T cells expressing CRBN and its mutants were prepared and immunopurification was performed as described above.

(8) Immunostaining

HeLa cells overexpressing CRBN and DDB1 fused with the HA or V5 tags were fixed and mixed with anti-HA and anti-V5 antibody, and react with secondary antibodies conjugated to Alexa Fluor 594 or 488 (Invitrogen), respectively.

(9) In Vitro Ubiquitination Assay

In vitro ubiquitination assays were performed as described (Cited Literature 37). FH-CRBN complex (200 ng) was incubated at 30° C. for two hours in the 15 µl of buffer containing 500 ng of Uba 1 (Biomol), 500 ng of UbCH5b (Biomol), 4000 ng of GST-Ubiquitin (Calbiochem), and 4 mM ATP. Reactions were terminated by adding SDS and heating at 98° C. for five minutes.

(10) Autoubiquitination in Live Cells

The assays were performed as described (Cited Literature 38). 293T cells stably expressing FH-CRBN or its mutant were treated with 10 µM MG132 or DMSO (vehicle) for three hours. The cells lysate were prepared using RIPA buffer containing 25 µM MG132 and 10 mM N-ethylmaleimide. FH-CRBN was immunoprecipitated and analyzed as described above. Various concentrations of thalidomide were added to cells one hour prior to MG132 treatment.

(11) RNAi

The following Stealth RNAi oligonucleotides (Invitrogen) were used.

```
                                            (SEQ ID NO: 1)
DDB1 #1:     5'-CAUACCUUGAUAAUGGUGUUGUGUU-3'

(SEQ ID NO: 2)
DDB1 #2:     5'-CAGUAAUGAACAAGGCUCCUAUGUA-3'

(SEQ ID NO: 3)
Cul4A #1:    5'-GCAAAGCAUGUGGAUUCAAAGUUAA-3'

(SEQ ID NO: 4)
Cul4A #2:    5'-GAAUCUCUGAUAGACAGAGACUAUA-3'
```

Only sense strands are shown. As control, Stealth RNAi negative control of low GC content (Invitrogen) was used. 293T cells were transfected with 40 nM oligonucleotide using Lipofectamine RNAiMAX and harvested 72 hours later.

(12) Zebrafish

Fish were kept at 28.5° C. on a 14-hour light/10-hour dark cycle.

Embryos were obtained from natural matings (Cited Literature 35). The methods of alcian blue staining, microinjection and in situ hybridization are described in the following paragraphs. Zebrafish CRBN and Cul4A (zcrbn and zcul4a) genes were termed according to Zebrafish Nomenclature Guidelines by Zebrafish Nomenclature Committee.

(13) Thalidomide Treatment of Zebrafish

Thalidomide was dissolved in DMSO and added to a final concentration of 400 µM to E3 medium prewarmed to 65° C. Zebrafish embryos were dechorionated prior to thalidomide as follows: At 2 hpf, the embryos were incubated in E3 medium containing 2 mg/ml Protease type XIV (Sigma) for three minutes and then washed five times with the medium. After dechorionation, embryos were immediately transferred to E3 medium containing thalidomide, and observed for three days. The thalidomide-containing medium was exchanged every 12 hours.

(14) Alcian Blue Staining

Extracellular matrices associated with chondrocytes were stained with Alcian blue (Cited Literature 40). Zebrafish embryos were fixed in 3.7% neutral buffered formaldehyde for overnight. The next day, the embryos were washed with 100% ethanol and rehydrated with PBS. Subsequently, the embryos were incubated with a solution of 0.05% trypsin in saturated sodium tetraborate for one to three hours. Pigmentation of fish was removed by 3% hydrogen peroxide/1% potassium hydroxide solution. Stained embryos were stored in 70% glycerol-containing PBS solution.

(15) Microinjection of Antisense Morpholino Oligonucleotides and mRNA

Microinjection into one-cell stage embryos was carried out in accordance with Cited Literature 39. The present inventors used a nitrogen gas-pressure microinjector (IM 300, Narishige Co., Ltd.) for injection. Capped mRNAs were prepared in vitro using the mMESSAGE mMACHINE in vitro transcription kit (Ambion).

RNAs were dissolved in nuclease-free water at 600 ng/µl immediately before use. Antisense oligonucleotides (Gene Tools) used have the following sequences.

```
                            (SEQ ID NO: 5)
zCrbn AMO:    5'-AGAGCTGTAGCTGGTTCCCCATTTC-3'

(SEQ ID NO: 6)
zCul4A AMO:   5'-CTGGTGCTGAACATCTTCTGCCATC-3'
```

The concentrations of these oligos were dissolved in with nuclease-free water at 700 µM.

(16) Whole-Mount In Situ Hybridization

This assay was carried out in accordance with Cited Literature 41. Antisense probe for zcrbn mRNA was directed against the 5'-coding region of 513 bp. Antisense probe for zcul4a was directed against the 3' untranslated region (3' UTR) of 590 bp. Probes for shh and fgf8 were kindly provided by Dr. Krauss and Dr. Thisse, respectively. To increase permeability of probes, fixed embryos were incubated with PBS containing 0.1% Tween-20 and 10 mg/ml proteinase K for two minutes at room temperature.

(17) Measurement of Otic Vesicle Size

Zebrafish embryos at 48 hpf were anesthetized with 1% methylcellulose and 0.003% 3-amino benzoic acid ethyl ester (Sigma) and mounted on a slide glass. Then, otic vesicles of ten embryos randomly selected from each sample were photographed. The size was measured using the NIH image J software and compared to that of control. Average sizes and standard errors were calculated, and p-values were determined by the Mann-Whitney U test.

CITED LITERATURE LIST

Cited Literature 1: M. T. Miller, K. Stromland, Teratology 60, 306 (1999).
Cited Literature 2: M. Melchert, A. List, Int. J. Biochem. Cell Biol. 39, 1489 (2007).
Cited Literature 3: J. Knobloch, U. Ruther, Cell Cycle 7, 1121 (2008).
Cited Literature 4: T. Parman, M. J. Wiley, P. G. Wells, Nat. Med. 5, 582 (1999).
Cited Literature 5: R. J. D'Amato, M. S. Loughnan, E. Flynn, J. Folkman, Proc. Natl. Acad. Sci. U.S.A. 91, 4082 (1994).
Cited Literature 6: J. Sheskin, Clin. Pharmacol. Ther. 6, 303 (1965).
Cited Literature 7: S. Singhal et al., N. Engl. J. Med. 341, 1565 (1999).
Cited Literature 8: J. B. Zeldis, B. A. Williams, S. D. Thomas, M. E. Elsayed, Clin. Ther. 21, 319 (1999).
Cited Literature 9: S. Sakamoto, Y. Kabe, M. Hatakeyama, Y. Yamaguchi, H. Handa, Chem. Rec. 9, 66 (2009).
Cited Literature 10: S. Sakamoto, Y. Kabe, M. Hatakeyama, Y. Yamaguchi, H. Handa, Chem. Rec. 9, 66 (2009).
Cited Literature 11: J. J. Higgins, J. Pucilowska, R. Q. Lombardi, J. P. Rooney, Neurology 63, 1927 (2004).
Cited Literature 12: S. Angers et al., Nature 443, 590 (2006).
Cited Literature 13: R. Groisman et al., Cell 113, 357 (2003).
Cited Literature 14: F. Ohtake et al., Nature 446, 562 (2007).
Cited Literature 15: C. M. Pickart, Cell 116, 181 (2004).
Cited Literature 16: M. D. Petroski, R. J. Deshaies, Nat. Rev. Mol. Cell. Biol. 6, 9 (2005).
Cited Literature 17: K. Sugasawa et al., Cell 121, 387 (2005).
Cited Literature 18: R. Groisman et al., Genes Dev. 20, 1429 (2006).
Cited Literature 19: O. Leupin, S. Bontron, M. Strubin, J. Virol. 77, 6274 (2003).
Cited Literature 20: J. Jin, E. E. Arias, J. Chen, J. W. Harper, J. C. Walter, Mol. Cell. 23, 709 (2006).
Cited Literature 21: A. Nasevicius, S. C. Ekker, Nat. Genet. 26, 216 (2000).
Cited Literature 22: M. B. Veldman, S. Lin, Pediatr. Res. 64, 470 (2008).
Cited Literature 23: T. Yabu et al., Blood 106, 125 (2005).
Cited Literature 24: M. Tanaka et al., Nature 416, 527 (2002).
Cited Literature 25: M. C. Davis, R. D. Dahn, N. B. Shubin, Nature 447, 473 (2007).
Cited Literature 26: A. Streit, J. Anat. 199, 99 (2001).
Cited Literature 27: R. D. Riddle, R. L. Johnson, E. Laufer, C. Tabin, Cell 75, 1401 (1993).
Cited Literature 28: A. M. Moon, M. R. Capecchi, Nat. Genet. 26, 455 (2000).
Cited Literature 29: M. Lewandoski, X. Sun, G. R. Martin, Nat. Genet. 26, 460 (2000).
Cited Literature 30: A. L. Moreira et al., J. Exp. Med. 177, 1675 (1993).
Cited Literature 31: D. Gupta et al., Leukemia 15, 1950 (2001).
Cited Literature 32: J. Knobloch, J. D. Shaughnessy, Jr., U. Ruther, FASEB J. 21, 1410 (2007).
Cited Literature 33: T. Kamura, C. S. Brower, R. C. Conaway, J. W. Conaway, J. Biol. Chem. 277, 30388 (2002).
Cited Literature 34: J. M. Hansen, S. G. Gong, M. Philbert, C. Harris, Dev. Dyn. 225, 186 (2002).
Cited Literature 35: S. Pajni-Underwood, C. P. Wilson, C. Elder, Y. Mishina, M. Lewandoski, Development 134, 2359 (2007).
Cited Literature 36: H. Uga et al., Mol. Pharmacol. 70, 1832 (2006).
Cited Literature 37: R. Groisman et al., Cell 113, 357 (2003).
Cited Literature 38: F. Ohtake et al., Nature 446, 562 (2007).
Cited Literature 39: H. Ando, T. Furuta, H. Okamoto, Methods Cell Biol. 77, 159 (2004).
Cited Literature 40: W. L. Kelly, M. M. Bryden, Stain Technol. 58, 131 (1983).
Cited Literature 41: C. Thisse, B. Thisse, Nat. Protoc. 3, 59 (2008).

INDUSTRIAL APPLICABILITY

The present invention can be utilized for determining whether a test substance has thalidomide-like teratogenicity, and thus can be utilized for development of alternative medicines to thalidomide and medicines capable of suppressing the thalidomide-induced teratogenicity.

The invention claimed is:

1. A screening method for a substance that does not have thalidomide-like teratogenicity comprising:
    bringing a test substance into contact with cereblon or a fragment of cereblon, and
    selecting a test substance that does not bind to cereblon or the fragment of cereblon or a test substance which has a lower affinity for cereblon as compared with thalidomide under similar conditions,
    wherein cereblon or the fragment of cereblon have a sequence selected from the group of sequences consisting of SEQ ID NO:12, SEQ ID NO:13, SEQ ID NO:14, SEQ ID NO:15 and SEQ ID NO:16, and
    wherein when the test substance does not bind to cereblon or the fragment of cereblon, or has lower affinity for cereblon or the fragment of cereblon as compared with thalidomide, the test substance is determined to not have thalidomide-like teratogenicity.

2. The screening method for a substance that does not have thalidomide-like teratogenicity according to claim 1, wherein the test substance is a medicine.

3. The screening method for a substance that does not have thalidomide-like teratogenicity according to claim 1, wherein the test substance is a thalidomide derivative of general formula (1):

[Formula 1]

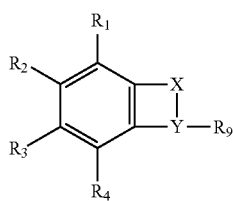

(1)

wherein, a compound in which X is $R_5$ to $R_7$ and Y is $R_6$ to $R_8$ is called Compound (A), a compound in which X is $R_5$ and Y is $R_6$ to $R_8$ is called Compound (B), and a compound in which X is $R_5$ and Y is $R_8$ is called Compound (C), and $R_1$, $R_2$, $R_3$ and $R_4$ are each selected from —H; —OH; =O; linear and branched alkane, alkene and alkyne; cyclic alkane, alkene and alkyne; a combination of cyclic and non-cyclic alkane, alkene and alkyne; alcohol, aldehyde, ketone, carboxylic acid, ester or an ether moiety combining a ring and a non-ring or a combination of cyclic/non-cyclic moieties; aza; amino; -MOn or —O-MOn [wherein, M=N and n=2; M=S and n=2 or 3; or M=P and n=1 to 3]; and halogen; and $R_5$, $R_6$, $R_7$ and $R_8$ are each independently selected from the formula (2):

[Formula 2]

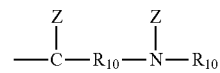

(2)

and —O— (wherein, Z is optional and defined in the same way as $R_1$ as described above); and $R_{10}$ is defined in the same way as $R_1$ as described above, or, (when Z is non-existent), $R_{10}$=O;

$R_9$ is a moiety having the formula (3), (4), (5), (6) or (7):

[Formula 3]

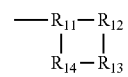

(3)

-continued

[Formula 4]

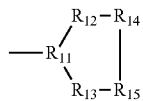
(4)

[Formula 5]

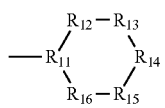
(5)

[Formula 6]

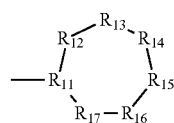
(6)

wherein, $R_1$ to $R_{17}$ are each (independently) defined in the same way as $R_5$ as described above, or

[Formula 7]

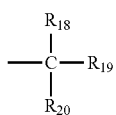
(7)

wherein, $R_{18}$, $R_{19}$ and $R_{20}$ are each independently selected from
H, —$CH_3$, —COOH, —$CONH_2$, —$(CH_2)_n$—COOH and —$(CH_2)_n CONH_2$,
wherein n 1 to 4, and
wherein the test substance is not thalidomide.

4. The screening method for a substance that does not have thalidomide-like teratogenicity according, to claim 3, wherein the thalidomide derivative has pharmacological actions of thalidomide or a known thalidomide derivative.

5. The screening method for a substance that does not have thalidomide-like teratogenicity according to claim 1, wherein the cereblon or the fragment of cereblon is immobilized on a carrier.

6. The screening method for a substance that does not have thalidomide-like teratogenicity according to claim 1, wherein the cereblon has a sequence selected from the group of sequences consisting of SEQ ID NO:7, SEQ ID NO:8, SEQ NO:9, SEQ NO:10, and SEQ ID NO:11.

7. A screening method for an antagonist of a substance that does not have thalidomide-like teratogenicity comprising:
    bringing a test substance into contact with cereblon or a fragment of cereblon,
    selecting a test substance that binds to cereblon or the fragment of cereblon, and
    selecting, from among the substances selected by the above step, a substance capable of reducing
        i) teratogenicity, or
        ii) an inhibitory action exerted on an activity of a cereblon-containing ubiquitin ligase complex,
    wherein the cereblon or the fragment of cereblon has a sequence selected from the group consisting of SEQ ID NO: 12, SEQ ID NO: 13, SEQ ID NO: 14, SEQ ID NO: 15 and SEQ ID NO: 16,
    wherein the fragment of cereblon binds thalidomide under similar conditions, and
    wherein when the test substance does not bind to cereblon or the fragment of cereblon, or has lower affinity for cereblon or the fragment of cereblon as compared with thalidomide, the test substance is determined to not have thalidomide-like teratogenicity.

8. The screening method for an antagonist of a substance that does not have thalidomide-like teratogenicity according to claim 7, wherein the cereblon or the fragment of cereblon is immobilized on a carrier.

9. The screening method for an antagonist of a substance that does not have thalidomide-like teratogenicity according to claim 7, wherein the cereblon has a sequence selected from the group of sequences consisting of SEQ ID NO: 7 SEQ ID NO: 8, SEQ ID NO: 9, SEQ ID NO: 10 and SEQ ID NO: 11.

10. A mutated cereblon comprising the following amino acid substitution (a) and/or (b);
    (a) substitution of tyrosine at position 384 from the N-terminus of human cereblon having a sequence of SEQ ID NO: 7 or an equivalent amino acid with alanine; and
    (b) substitution of tryptophan at position 386 from the N-terminus of human cereblon having a sequence or SEQ ID NO: 7 an equivalent amino acid with alanine.

11. An isolated at nucleic acid encoding the mutated cereblon according to claim 10.

12. A thalidomide induced teratogenicity-resistant non-human animal having introduced therein the nucleic acid encoding mutated cereblon according to claim 11.

* * * * *